US010336815B2

(12) United States Patent
Yang et al.

(10) Patent No.: US 10,336,815 B2
(45) Date of Patent: Jul. 2, 2019

(54) PHAGE-DISPLAYED ANTIBODY LIBRARIES AND USES THEREOF

(71) Applicant: Academia Sinica, Taipei (TW)

(72) Inventors: An-Suei Yang, Taipei (TW); Ing-Chien Chen, Taipei (TW); Chao-Ping Tung, Taipei (TW); Chung-Ming Yu, Taipei (TW)

(73) Assignee: Academia Sinica, Taipei (TW)

( * ) Notice: Subject to any disclaimer, the term of this patent is extended or adjusted under 35 U.S.C. 154(b) by 63 days.

(21) Appl. No.: 15/232,819

(22) Filed: Aug. 10, 2016

(65) Prior Publication Data
US 2017/0044239 A1 Feb. 16, 2017

Related U.S. Application Data

(60) Provisional application No. 62/204,966, filed on Aug. 13, 2015.

(51) Int. Cl.

*C07K 16/00* (2006.01)
*C07K 16/10* (2006.01)
*C12N 15/10* (2006.01)

(52) U.S. Cl.
CPC ........ *C07K 16/005* (2013.01); *C07K 16/1018* (2013.01); *C12N 15/1037* (2013.01); *C07K 2317/33* (2013.01); *C07K 2317/34* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS 9,527,924 B2 * 12/2016 Marasco ............ C07K 16/1018

OTHER PUBLICATIONS

Sui et al. Structural and functional bases for broad-spectrum neutralization of avian and human influenza A viruses. Nat Struct Mol Biol. Mar. 2009;16(3):265-73. (Year: 2009).*
Pansri et al. A compact phage display human scFv library for selection of antibodies to a wide variety of antigens. BMC Biotechnol. Jan. 29, 2009;9:6. (Year: 2009).*
Chao-Ping Tung et al.; Scientific Reports, Discovering neutralizing antibodies targeting the stem epitope of H1N1 influenza hemagglutinin with synthetic phagedisplayed antibody libraries, 2015, 5: 15053.

* cited by examiner

*Primary Examiner* — Michelle S Horning

(57) ABSTRACT

Disclosed herein are phage-displayed single-chain variable fragment (scFv) libraries, which comprised a plurality of scFvs with a specific sequence in each CDR. The present scFv libraries could be used to efficiently produce different antibodies with high binding affinity to H1 hemagglutinin of influenza virus. Accordingly, the present disclosure provides a potential means to generate different antigen-specific antibodies promptly in accordance with the need in experimental researches and/or clinical applications.

8 Claims, 10 Drawing Sheets

Specification includes a Sequence Listing.

SEQUENCE LISTING

```
<160> NUMBER OF SEQ ID NOS: 73

<210> SEQ ID NO 1
<211> LENGTH: 45
<212> TYPE: DNA
<213> ORGANISM: Artificial Sequence
<220> FEATURE:
<223> OTHER INFORMATION: CDR-H1 library
<220> FEATURE:
<221> NAME/KEY: variation
<222> LOCATION: 10,11,13,14,16,17,19,20,22,23,25,26,28,29,31,32,34,35
<223> OTHER INFORMATION: /note="n is any of A, T, C, or G"

<400> SEQUENCE: 1
agctgtaccn nknnknnknn knnknnknnk nnknnkgcaa ttagc              45

<210> SEQ ID NO 2
<211> LENGTH: 36
<212> TYPE: DNA
<213> ORGANISM: Artificial Sequence
<220> FEATURE:
<223> OTHER INFORMATION: CDR-H2 library
<220> FEATURE:
<221> NAME/KEY: variation
<222> LOCATION: 10,11,13,14,16,17,19,20,22,23,25,26
<223> OTHER INFORMATION: /note="n is any of A, T, C, or G"

<400> SEQUENCE: 2
ggtggtattn nknnknnknn knnknnkccg aattat                         36

<210> SEQ ID NO 3
<211> LENGTH: 42
```

```
<212> TYPE: DNA
<213> ORGANISM: Artificial Sequence
<220> FEATURE:
<223> OTHER INFORMATION: CDR-H3 library
<220> FEATURE:
<221> NAME/KEY: variation
<222> LOCATION: 4,5,7,8,10,11,13,14,16,17,19,20,22,23,25,26,28,29,31,32
<223> OTHER INFORMATION: /note="n is any of A, T, C, or G"

<400> SEQUENCE: 3
agcnnknnkn nknnknnknn knnknnknnk nnkgtttttg at                42

<210> SEQ ID NO 4
<211> LENGTH: 21
<212> TYPE: DNA
<213> ORGANISM: Artificial Sequence
<220> FEATURE:
<223> OTHER INFORMATION: CDR-H1
<220> FEATURE:
<221> NAME/KEY: variation
<222> LOCATION: 4,5,7,8,16,17
<223> OTHER INFORMATION: /note="n is any of A, T, C, or G"

<400> SEQUENCE: 4
gaannknnkt ttccgnnktt t                                       21

<210> SEQ ID NO 5
<211> LENGTH: 18
<212> TYPE: DNA
<213> ORGANISM: Artificial Sequence
<220> FEATURE:
<223> OTHER INFORMATION: CDR-H2
<220> FEATURE:
<221> NAME/KEY: variation
<222> LOCATION: 13,14,16,17
<223> OTHER INFORMATION: /note="n is any of A, T, C, or G"

<400> SEQUENCE: 5
agcccgatgt ttnnknnk                                           18

<210> SEQ ID NO 6
<211> LENGTH: 21
<212> TYPE: DNA
<213> ORGANISM: Artificial Sequence
<220> FEATURE:
<223> OTHER INFORMATION: CDR-H3
<220> FEATURE:
<221> NAME/KEY: variation
<222> LOCATION: 4,5,10,11,13,14,16,17,19,20
<223> OTHER INFORMATION: /note="n is any of A, T, C, or G"

<400> SEQUENCE: 6
ccgnnktatn nknnknnknn k                                       21

<210> SEQ ID NO 7
<211> LENGTH: 360
<212> TYPE: DNA
<213> ORGANISM: Artificial Sequence
<220> FEATURE:
<223> OTHER INFORMATION: F10 template

<400> SEQUENCE: 7
caggttcagc tggttcagag cggtgcagaa gttaaaaaac cgggtagcag cgttaaagtt    60
agctgtacca gcagcgaagt taccttttagc agctttgcaa ttagctgggt tcgtcaggca   120
ccgggtcagg gtctggaatg gctggtggt attagcccga tgtttggcac ccgaattat    180 gcacagaaat ttcagggtcg tgttaccatt accgcagatc agagcacccg taccgcatat   240
```

```
atggatctgc gtagcctgcg tagtgaagat accgcagtgt attattgtgc acgtagcccg    300
agctatattt gtagcggtgg cacctgtgtt tttgatcatt ggggtcaggg caccctggtg    360
```

<210> SEQ ID NO 8
<211> LENGTH: 55
<212> TYPE: DNA
<213> ORGANISM: Artificial Sequence
<220> FEATURE:
<223> OTHER INFORMATION: Template_1 primer

<400> SEQUENCE: 8

```
gctgtaccag cagcgaagtt taataagaat tctttgcaat tagctgggtt cgtca    55
```

<210> SEQ ID NO 9
<211> LENGTH: 70
<212> TYPE: DNA
<213> ORGANISM: Artificial Sequence
<220> FEATURE:
<223> OTHER INFORMATION: F10-CDRH1_1 primer
<220> FEATURE:
<221> NAME/KEY: variation
<222> LOCATION: 23,24,26,27,29,30,32,33,35,36,38,39,41,42,44,45,47,48
<223> OTHER INFORMATION: /note="n is any of A, T, C, or G"

<400> SEQUENCE: 9

```
cagcgttaaa gttagctgta ccnnknnknn knnknnknnk nnknnknnkg caattagctg    60
ggttcgtcag                                                           70
```

<210> SEQ ID NO 10
<211> LENGTH: 54
<212> TYPE: DNA
<213> ORGANISM: Artificial Sequence
<220> FEATURE:
<223> OTHER INFORMATION: Template_2 primer

<400> SEQUENCE: 10

```
ctgggtggta ttagcccgta ataagaattc ccgaattatg cacagaaatt tcag    54
```

<210> SEQ ID NO 11
<211> LENGTH: 63
<212> TYPE: DNA
<213> ORGANISM: Artificial Sequence
<220> FEATURE:
<223> OTHER INFORMATION: F10-CDRH2_1 primer
<220> FEATURE:
<221> NAME/KEY: variation
<222> LOCATION: 22,23,25,26,28,29,31,32,34,35,37,38
<223> OTHER INFORMATION: /note="n is any of A, T, C, or G"

<400> SEQUENCE: 11

```
ctggaatggc tgggtggtat tnnknnknnk nnknnknnkc cgaattatgc acagaaattt    60
cag                                                                  63
```

<210> SEQ ID NO 12
<211> LENGTH: 57
<212> TYPE: DNA
<213> ORGANISM: Artificial Sequence
<220> FEATURE:
<223> OTHER INFORMATION: Template_3 primer

<400> SEQUENCE: 12

```
acgtagcccg agctatattt gttaataaga attctgtgtt tttgatcatt ggggtca    57
```

<210> SEQ ID NO 13
<211> LENGTH: 75

```
<212> TYPE: DNA
<213> ORGANISM: Artificial Sequence
<220> FEATURE:
<223> OTHER INFORMATION: F10-CDRH3_1 primer
<220> FEATURE:
<221> NAME/KEY: variation
<222> LOCATION: 24,25,27,28,30,31,33,34,36,37,39,40,42,43,45,46,48,49,
      51,52
<223> OTHER INFORMATION: /note="n is any of A, T, C, or G"

<400> SEQUENCE: 13
cagtgtatta ttgtgcacgt agcnnknnkn nknnknnknn knnknnknnk nnkgttttg      60 atcattgggg tcagg                                                     75

<210> SEQ ID NO 14
<211> LENGTH: 64
<212> TYPE: DNA
<213> ORGANISM: Artificial Sequence
<220> FEATURE:
<223> OTHER INFORMATION: F10-CDRH123_1 primer
<220> FEATURE:
<221> NAME/KEY: V_region
<222> LOCATION: 28,29,31,32,40,41
<223> OTHER INFORMATION: /note="n is any of A, T, C, or G"

<400> SEQUENCE: 14
gttaaagtta gctgtaccag cagcgaannk nnktttccgn nktttgcaat tagctgggtt    60
cgtc                                                                 64

<210> SEQ ID NO 15
<211> LENGTH: 55
<212> TYPE: DNA
<213> ORGANISM: Artificial Sequence
<220> FEATURE:
<223> OTHER INFORMATION: F10-CDRH123_2 primer
<220> FEATURE:
<221> NAME/KEY: variation
<222> LOCATION: 26,27,29,30
<223> OTHER INFORMATION: /note="n is any of A, T, C, or G"

<400> SEQUENCE: 15
gctgggtggt attagcccga tgtttnnknn kccgaattat gcacagaaat ttcag         55

<210> SEQ ID NO 16
<211> LENGTH: 62
<212> TYPE: DNA
<213> ORGANISM: Artificial Sequence
<220> FEATURE:
<223> OTHER INFORMATION: F10-CDRH123_3 primer
<220> FEATURE:
<221> NAME/KEY: variation
<222> LOCATION: 23,24,29,30,32,33,35,36,38,39
<223> OTHER INFORMATION: /note="n is any of A, T, C, or G"

<400> SEQUENCE: 16
gtattattgt gcacgtagcc cgnnktatnn knnknnknnk gttttgatc attggggtca     60 gg                                                                   62

<210> SEQ ID NO 17
<211> LENGTH: 43
<212> TYPE: PRT
<213> ORGANISM: Artificial Sequence
<220> FEATURE:
<223> OTHER INFORMATION: gp67 signal peptide

<400> SEQUENCE: 17

Met Leu Leu Val Asn Gln Ser His Gln Gly Phe Asn Lys Glu His Thr
```

```
            1               5                  10                  15
Ser Lys Met Val Ser Ala Ile Val Leu Tyr Val Leu Leu Ala Ala Ala
                      20                  25                  30

Ala His Ser Ala Phe Ala Ala Asp Leu Ala Ser
        35                  40
```

<210> SEQ ID NO 18
<211> LENGTH: 45
<212> TYPE: PRT
<213> ORGANISM: Artificial Sequence
<220> FEATURE:
<223> OTHER INFORMATION: C-terminal thrombin cutting site, trimerization
      domain and His6-tag

<400> SEQUENCE: 18

```
Ala Ser Leu Val Pro Arg Gly Ser Pro Gly Ser Gly Tyr Ile Pro Glu
1               5                  10                  15

Ala Pro Arg Asp Gly Gln Ala Tyr Val Arg Lys Asp Gly Glu Trp Val
                20                  25                  30

Leu Leu Ser Thr Phe Leu Gly His His His His His His
            35                  40                  45
```

<210> SEQ ID NO 19
<211> LENGTH: 15
<212> TYPE: PRT
<213> ORGANISM: Artificial Sequence
<220> FEATURE:
<223> OTHER INFORMATION: Avitag oligopeptide

<400> SEQUENCE: 19

```
Gly Leu Asn Asp Ile Phe Glu Ala Gln Lys Ile Glu Trp His Glu
1               5                  10                  15
```

<210> SEQ ID NO 20
<211> LENGTH: 47
<212> TYPE: DNA
<213> ORGANISM: Artificial Sequence
<220> FEATURE:
<223> OTHER INFORMATION: VL forward primer

<400> SEQUENCE: 20
ccaggtgcac gatgtgatgg taccgatatt caaatgaccc agagccc          47

<210> SEQ ID NO 21
<211> LENGTH: 36
<212> TYPE: DNA
<213> ORGANISM: Artificial Sequence
<220> FEATURE:
<223> OTHER INFORMATION: VL reverse primer

<400> SEQUENCE: 21
tgcagccacc gtgcgtttga tttccacttt ggtgcc                      36

<210> SEQ ID NO 22
<211> LENGTH: 34
<212> TYPE: DNA
<213> ORGANISM: Artificial Sequence
<220> FEATURE:
<223> OTHER INFORMATION: VH forward primer

<400> SEQUENCE: 22
cgtgtcgcat ctgaagtgca gctggtggaa tcgg                        34

<210> SEQ ID NO 23
<211> LENGTH: 46
<212> TYPE: DNA
<213> ORGANISM: Artificial Sequence
<220> FEATURE:
<223> OTHER INFORMATION: VH reverse primer

<400> SEQUENCE: 23
gaccgatggg cccttggtgc tagccgagct cacggtaaca agggtg           46

<210> SEQ ID NO 24
<211> LENGTH: 124
<212> TYPE: PRT
<213> ORGANISM: Artificial Sequence
<220> FEATURE:
<223> OTHER INFORMATION: H2-143 variant

<400> SEQUENCE: 24

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe His Gln Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120
```

<210> SEQ ID NO 25
<211> LENGTH: 124
<212> TYPE: PRT
<213> ORGANISM: Artificial Sequence
<220> FEATURE:
<223> OTHER INFORMATION: H2-165 variant

<400> SEQUENCE: 25

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Ala Phe Asn His Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
```

-continued 115           120

<210> SEQ ID NO 26
<211> LENGTH: 124
<212> TYPE: PRT
<213> ORGANISM: Artificial Sequence
<220> FEATURE:
<223> OTHER INFORMATION: H3-143 variant

<400> SEQUENCE: 26

Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Leu Gly Gln Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120

<210> SEQ ID NO 27
<211> LENGTH: 124
<212> TYPE: PRT
<213> ORGANISM: Artificial Sequence
<220> FEATURE:
<223> OTHER INFORMATION: H2-26 variant

<400> SEQUENCE: 27

Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gln Met Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120

<210> SEQ ID NO 28
<211> LENGTH: 124
<212> TYPE: PRT
<213> ORGANISM: Artificial Sequence
<220> FEATURE:
<223> OTHER INFORMATION: H2-55 variant

<400> SEQUENCE: 28

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gln Ile Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Thr Cys Val Phe Asp
            100                 105                 110

His Trp Gly Gln Gly Thr Leu Val Thr Val Ser Ser
        115                 120
```

<210> SEQ ID NO 29
<211> LENGTH: 124
<212> TYPE: PRT
<213> ORGANISM: Artificial Sequence
<220> FEATURE:
<223> OTHER INFORMATION: H2-181 variant

<400> SEQUENCE: 29

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Leu Phe Gln Ile Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Thr Cys Val Phe Asp
            100                 105                 110

His Trp Gly Gln Gly Thr Leu Val Thr Val Ser Ser
        115                 120
```

<210> SEQ ID NO 30
<211> LENGTH: 124
<212> TYPE: PRT
<213> ORGANISM: Artificial Sequence
<220> FEATURE:
<223> OTHER INFORMATION: H2-167 variant

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45
```

Gly Gly Ile Ala Pro Ala Phe Asn Leu Pro Asn Tyr Ala Gln Lys Phe
            50                  55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                 85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
            115                 120

<210> SEQ ID NO 31
<211> LENGTH: 124
<212> TYPE: PRT
<213> ORGANISM: Artificial Sequence
<220> FEATURE:
<223> OTHER INFORMATION: H2-63 variant

<400> SEQUENCE: 31

Gln Val Gln Leu Val Gln Ser Gly Ala Glu Val Lys Lys Pro Gly Ser
 1               5                  10                  15

Ser Val Lys Val Ser Cys Thr Ser Ser Glu Val Thr Phe Ser Ser Phe
                 20                  25                  30

Ala Ile Ser Trp Val Arg Gln Ala Pro Gly Gln Gly Leu Glu Trp Leu
             35                  40                  45

Gly Gly Ile Ser Met Met Phe Asn Gln Pro Asn Tyr Ala Gln Lys Phe
            50                  55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                 85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
            115                 120

<210> SEQ ID NO 32
<211> LENGTH: 124
<212> TYPE: PRT
<213> ORGANISM: Artificial Sequence
<220> FEATURE:
<223> OTHER INFORMATION: H3-142 variant

<400> SEQUENCE: 32

Gln Val Gln Leu Val Gln Ser Gly Ala Glu Val Lys Lys Pro Gly Ser
 1               5                  10                  15

Ser Val Lys Val Ser Cys Thr Ser Ser Glu Val Thr Phe Ser Ser Phe
                 20                  25                  30

Ala Ile Ser Trp Val Arg Gln Ala Pro Gly Gln Gly Leu Glu Trp Leu
             35                  40                  45

Gly Gly Ile Ser Pro Gln Phe Pro Arg Pro Asn Tyr Ala Gln Lys Phe
            50                  55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                 85                  90                  95

Ala Arg Ser Pro Ser Tyr Ile Cys Ser Gly Gly Thr Cys Val Phe Asp 100                 105                 110

His Trp Gly Gln Gly Thr Leu Val Thr Val Ser Ser
        115                 120

<210> SEQ ID NO 33
<211> LENGTH: 124
<212> TYPE: PRT
<213> ORGANISM: Artificial Sequence
<220> FEATURE:
<223> OTHER INFORMATION: H2-64 variant

<400> SEQUENCE: 33

Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
                20                  25                  30

Ala Ile Ser Trp Val Arg Gln Ala Pro Gly Gln Gly Leu Glu Trp Leu
            35                  40                  45

Gly Gly Ile Ser Met Met Phe Asn Gln Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
                100                 105                 110

His Trp Gly Gln Gly Thr Leu Val Thr Val Ser Ser
        115                 120

<210> SEQ ID NO 34
<211> LENGTH: 124
<212> TYPE: PRT
<213> ORGANISM: Artificial Sequence
<220> FEATURE:
<223> OTHER INFORMATION: H1-62 variant

<400> SEQUENCE: 34

Gln Val Gln Leu Val Gln Ser Gly Ala Glu Val Lys Lys Pro Gly Ser
1               5                   10                  15

Ser Val Lys Val Ser Cys Thr Tyr Asn Thr Ala Met Phe Pro Phe Tyr
                20                  25                  30

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
                100                 105                 110

His Trp Gly Gln Gly Thr Leu Val Thr Val Ser Ser
        115                 120

<210> SEQ ID NO 35
<211> LENGTH: 124
<212> TYPE: PRT
<213> ORGANISM: Artificial Sequence
<220> FEATURE:

<223> OTHER INFORMATION: H3-141 variant

<400> SEQUENCE: 35

Gln Val Gln Leu Val Gln Ser Gly Ala Glu Val Lys Lys Pro Gly Ser
1               5                   10                  15

Ser Val Lys Val Ser Cys Thr Tyr Asp Thr Met Ser Phe Met Phe Tyr
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120

<210> SEQ ID NO 36
<211> LENGTH: 124
<212> TYPE: PRT
<213> ORGANISM: Artificial Sequence
<220> FEATURE:
<223> OTHER INFORMATION: H3-132 variant

<400> SEQUENCE: 36

Gln Val Gln Leu Val Gln Ser Gly Ala Glu Val Lys Lys Pro Gly Ser
1               5                   10                  15

Ser Val Lys Val Ser Cys Thr Ser Asn Glu Gln Leu Phe Gln His Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120

<210> SEQ ID NO 37
<211> LENGTH: 124
<212> TYPE: PRT
<213> ORGANISM: Artificial Sequence
<220> FEATURE:
<223> OTHER INFORMATION: H1-74 variant

<400> SEQUENCE: 37

Gln Val Gln Leu Val Gln Ser Gly Ala Glu Val Lys Lys Pro Gly Ser
1               5                   10                  15

Ser Val Lys Val Ser Cys Thr Trp Ser Gly Leu Phe Phe Ser Ala Asn
            20                  25                  30

Ala Ile Ser Trp Val Arg Gln Ala Pro Gly Gln Gly Leu Glu Trp Leu

```
                35                  40                  45
Gly Gly Ile Ser Pro Met Phe Gly Thr Pro Asn Tyr Ala Gln Lys Phe
 50                  55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                 85                  90                  95

Ala Arg Ser Pro Ser Tyr Ile Cys Ser Gly Gly Thr Cys Val Phe Asp
                100                 105                 110

His Trp Gly Gln Gly Thr Leu Val Thr Val Ser Ser
            115                 120

<210> SEQ ID NO 38
<211> LENGTH: 124
<212> TYPE: PRT
<213> ORGANISM: Artificial Sequence
<220> FEATURE:
<223> OTHER INFORMATION: H1-82 variant

<400> SEQUENCE: 38

Gln Val Gln Leu Val Gln Ser Gly Ala Glu Val Lys Lys Pro Gly Ser
  1               5                  10                  15

Ser Val Lys Val Ser Cys Thr Asn Asp Arg Ile Asp Phe Pro Leu Thr
                 20                  25                  30

Ala Ile Ser Trp Val Arg Gln Ala Pro Gly Gln Gly Leu Glu Trp Leu
             35                  40                  45

Gly Gly Ile Ser Pro Met Phe Gly Thr Pro Asn Tyr Ala Gln Lys Phe
 50                  55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                 85                  90                  95

Ala Arg Ser Pro Ser Tyr Ile Cys Ser Gly Gly Thr Cys Val Phe Asp
                100                 105                 110

His Trp Gly Gln Gly Thr Leu Val Thr Val Ser Ser
            115                 120

<210> SEQ ID NO 39
<211> LENGTH: 124
<212> TYPE: PRT
<213> ORGANISM: Artificial Sequence
<220> FEATURE:
<223> OTHER INFORMATION: H1-81 variant

<400> SEQUENCE: 39

Gln Val Gln Leu Val Gln Ser Gly Ala Glu Val Lys Lys Pro Gly Ser
  1               5                  10                  15

Ser Val Lys Val Ser Cys Thr Asn Thr Thr Asn Ile Leu Met Ser Asp
                 20                  25                  30

Ala Ile Ser Trp Val Arg Gln Ala Pro Gly Gln Gly Leu Glu Trp Leu
             35                  40                  45

Gly Gly Ile Ser Pro Met Phe Gly Thr Pro Asn Tyr Ala Gln Lys Phe
 50                  55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                 85                  90                  95
```

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
            115                 120

<210> SEQ ID NO 40
<211> LENGTH: 124
<212> TYPE: PRT
<213> ORGANISM: Artificial Sequence
<220> FEATURE:
<223> OTHER INFORMATION: H1-80 variant

<400> SEQUENCE: 40

Gln Val Gln Leu Val Gln Ser Gly Ala Glu Val Lys Lys Pro Gly Ser
1               5                   10                  15

Ser Val Lys Val Ser Cys Thr Val Ile Asp Val Met Trp Gln Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
            115                 120

<210> SEQ ID NO 41
<211> LENGTH: 124
<212> TYPE: PRT
<213> ORGANISM: Artificial Sequence
<220> FEATURE:
<223> OTHER INFORMATION: H1-83 variant

<400> SEQUENCE: 41

Gln Val Gln Leu Val Gln Ser Gly Ala Glu Val Lys Lys Pro Gly Ser
1               5                   10                  15

Ser Val Lys Val Ser Cys Thr Thr Arg Asn Asp Phe Leu Tyr Trp Gln
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
            115                 120

<210> SEQ ID NO 42
<211> LENGTH: 124
<212> TYPE: PRT
<213> ORGANISM: Artificial Sequence -continued

```
<220> FEATURE:
<223> OTHER INFORMATION: H3-136 variant

<400> SEQUENCE: 42

Gln Val Gln Leu Val Gln Ser Gly Ala Glu Val Lys Lys Pro Gly Ser
1               5                   10                  15

Ser Val Lys Val Ser Cys Thr Ser Asn Gln Ile Ser Phe Thr Ser His
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120

<210> SEQ ID NO 43
<211> LENGTH: 124
<212> TYPE: PRT
<213> ORGANISM: Artificial Sequence
<220> FEATURE:
<223> OTHER INFORMATION: H3-139 variant

<400> SEQUENCE: 43

Gln Val Gln Leu Val Gln Ser Gly Ala Glu Val Lys Lys Pro Gly Ser
1               5                   10                  15

Ser Val Lys Val Ser Cys Thr Asp Tyr Ser Tyr Ser Tyr Gly Gln Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120

<210> SEQ ID NO 44
<211> LENGTH: 124
<212> TYPE: PRT
<213> ORGANISM: Artificial Sequence
<220> FEATURE:
<223> OTHER INFORMATION: H3-268 variant

<400> SEQUENCE: 44

Gln Val Gln Leu Val Gln Ser Gly Ala Glu Val Lys Lys Pro Gly Ser
1               5                   10                  15

Ser Val Lys Val Ser Cys Thr Ser Glu Val Thr Phe Ser Ser Phe
            20                  25                  30
```

```
Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
 50                      55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                85                  90                  95

Ala Arg Ser Pro Gln Tyr Ala Ile Pro Leu Ala Gly Val Phe Asp
                100                 105                 110

His Trp Gly Gln Gly Thr Leu Val Thr Val Ser Ser
            115                 120
```

<210> SEQ ID NO 45
<211> LENGTH: 124
<212> TYPE: PRT
<213> ORGANISM: Artificial Sequence
<220> FEATURE:
<223> OTHER INFORMATION: H3-48 variant

<400> SEQUENCE: 45

```
Gln Val Gln Leu Val Gln Ser Gly Ala Glu Val Lys Lys Pro Gly Ser
 1               5                   10                  15

Ser Val Lys Val Ser Cys Thr Ser Ser Glu Val Thr Phe Ser Ser Phe
                20                  25                  30

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
 50                      55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                85                  90                  95

Ala Arg Ser Pro Ser Tyr Asn Ala Thr Ile Ser Lys Gly Val Phe Asp
                100                 105                 110

His Trp Gly Gln Gly Thr Leu Val Thr Val Ser Ser
            115                 120
```

<210> SEQ ID NO 46
<211> LENGTH: 124
<212> TYPE: PRT
<213> ORGANISM: Artificial Sequence
<220> FEATURE:
<223> OTHER INFORMATION: H3-188 variant

<400> SEQUENCE: 46

```
Gln Val Gln Leu Val Gln Ser Gly Ala Glu Val Lys Lys Pro Gly Ser
 1               5                   10                  15

Ser Val Lys Val Ser Cys Thr Ser Ser Glu Val Thr Phe Ser Ser Phe
                20                  25                  30

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
 50                      55                  60

Gln Gly Arg Val Thr Ile Thr Ala Asp Gln Ser Thr Arg Thr Ala Tyr
 65                  70                  75                  80

Met Asp Leu Arg Ser Leu Arg Ser Glu Asp Thr Ala Val Tyr Tyr Cys
                85                  90                  95
```

Ala Arg Ser Pro Gln Tyr Gln Thr Ile Lys Gly Leu Gly Val Phe Asp
            100                 105                 110

His Trp Gly Gln Gly Thr Leu Val Thr Val Ser Ser
            115                 120

<210> SEQ ID NO 47
<211> LENGTH: 124
<212> TYPE: PRT
<213> ORGANISM: Artificial Sequence
<220> FEATURE:
<223> OTHER INFORMATION: H3-172 variant

<400> SEQUENCE: 47

Gln Val Gln Leu Val Gln Ser Gly Ala Glu Val Lys Lys Pro Gly Ser
1               5                   10                  15

Ser Val Lys Val Ser Cys Thr Ser Glu Val Thr Phe Ser Ser Phe
            20                  25                  30

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Asn Thr Ala Phe Ile Ala His Met Asn Ser Val Phe Asp
            100                 105                 110

His Trp Gly Gln Gly Thr Leu Val Thr Val Ser Ser
            115                 120

<210> SEQ ID NO 48
<211> LENGTH: 124
<212> TYPE: PRT
<213> ORGANISM: Artificial Sequence
<220> FEATURE:
<223> OTHER INFORMATION: H3-49 variant

<400> SEQUENCE: 48

Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Trp Tyr Thr Pro Ala Asn Ser Leu Ser Val Phe Asp
            100                 105                 110

His Trp Gly Gln Gly Thr Leu Val Thr Val Ser Ser
            115                 120

<210> SEQ ID NO 49
<211> LENGTH: 124
<212> TYPE: PRT

<213> ORGANISM: Artificial Sequence
<220> FEATURE:
<223> OTHER INFORMATION: H3-61 variant

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Asn Thr Thr Met Ser Asn Gly Val Phe Asp
            100                 105                 110

His Trp Gly Gln Gly Thr Leu Val Thr Val Ser Ser
        115                 120
```

<210> SEQ ID NO 50
<211> LENGTH: 124
<212> TYPE: PRT
<213> ORGANISM: Artificial Sequence
<220> FEATURE:
<223> OTHER INFORMATION: H3-205 variant

<400> SEQUENCE: 50

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Phe Ser Pro Thr Asn Ala Asp Ala Val Phe Asp
            100                 105                 110

His Trp Gly Gln Gly Thr Leu Val Thr Val Ser Ser
        115                 120
```

<210> SEQ ID NO 51
<211> LENGTH: 124
<212> TYPE: PRT
<213> ORGANISM: Artificial Sequence
<220> FEATURE:
<223> OTHER INFORMATION: H3-182 variant

<400> SEQUENCE: 51

```
Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30
```

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr His Val Met Pro His Val Gly Val Phe Asp
                100                 105                 110

His Trp Gly Gln Gly Thr Leu Val Thr Val Ser Ser
            115                 120

<210> SEQ ID NO 52
<211> LENGTH: 124
<212> TYPE: PRT
<213> ORGANISM: Artificial Sequence
<220> FEATURE:
<223> OTHER INFORMATION: H3-219 variant

<400> SEQUENCE: 52

Gln Val Gln Leu Val Gln Ser Gly Ala Glu Val Lys Lys Pro Gly Ser
1               5                   10                  15

Ser Val Lys Val Ser Cys Thr Ser Glu Val Thr Phe Ser Ser Phe
            20                  25                  30

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Leu Ser Phe Thr Cys Ser Thr Ala Cys His Val Phe Asp
                100                 105                 110

His Trp Gly Gln Gly Thr Leu Val Thr Val Ser Ser
            115                 120

<210> SEQ ID NO 53
<211> LENGTH: 124
<212> TYPE: PRT
<213> ORGANISM: Artificial Sequence
<220> FEATURE:
<223> OTHER INFORMATION: H3-186 variant

<400> SEQUENCE: 53

Gln Val Gln Leu Val Gln Ser Gly Ala Glu Val Lys Lys Pro Gly Ser
1               5                   10                  15

Ser Val Lys Val Ser Cys Thr Ser Glu Val Thr Phe Ser Ser Phe
            20                  25                  30

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys 85                  90                  95

Ala Arg Ser Pro Thr Tyr Ile Thr Gly Ser Asp Gly Ala Val Phe Asp
                100                 105                 110

His Trp Gly Gln Gly Thr Leu Val Thr Val Ser Ser
                115                 120

<210> SEQ ID NO 54
<211> LENGTH: 121
<212> TYPE: PRT
<213> ORGANISM: Artificial Sequence
<220> FEATURE:
<223> OTHER INFORMATION: H123#437 variant

<400> SEQUENCE: 54

Gln Val Gln Leu Val Gln Ser Gly Ala Glu Val Lys Lys Pro Gly Ser
1               5                   10                  15

Ser Val Lys Val Ser Cys Thr Ser Ser Glu Phe Met Phe Pro Ala Phe
                20                  25                  30

Ala Ile Ser Trp Val Arg Gln Ala Pro Gly Gln Gly Leu Glu Trp Leu
            35                  40                  45

Gly Gly Ile Ser Pro Met Phe Asp His Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Leu Pro Ser Gly Val Phe Asp His Trp Gly
                100                 105                 110

Gln Gly Thr Leu Val Thr Val Ser Ser
            115                 120

<210> SEQ ID NO 55
<211> LENGTH: 121
<212> TYPE: PRT
<213> ORGANISM: Artificial Sequence
<220> FEATURE:
<223> OTHER INFORMATION: 1101-178 variant

<400> SEQUENCE: 55

Gln Val Gln Leu Val Gln Ser Gly Ala Glu Val Lys Lys Pro Gly Ser
1               5                   10                  15

Ser Val Lys Val Ser Cys Thr Ser Ser Glu Leu Leu Phe Pro Tyr Phe
                20                  25                  30

Ala Ile Ser Trp Val Arg Gln Ala Pro Gly Gln Gly Leu Glu Trp Leu
            35                  40                  45

Gly Gly Ile Ser Pro Met Phe Asn Gln Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Ser Thr Lys Gly Val Phe Asp His Trp Gly
                100                 105                 110

Gln Gly Thr Leu Val Thr Val Ser Ser
            115                 120

<210> SEQ ID NO 56
<211> LENGTH: 121

```
<212> TYPE: PRT
<213> ORGANISM: Artificial Sequence
<220> FEATURE:
<223> OTHER INFORMATION: 3rd_0.5_4_09H

<400> SEQUENCE: 56

Gln Val Gln Leu Val Gln Ser Gly Ala Glu Val Lys Lys Pro Gly Ser
1               5                   10                  15

Ser Val Lys Val Ser Cys Thr Ser Ser Glu Leu Val Phe Pro Leu Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Asn Lys Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Leu Pro Arg His Val Phe Asp His Trp Gly
            100                 105                 110

Gln Gly Thr Leu Val Thr Val Ser Ser
        115                 120

<210> SEQ ID NO 57
<211> LENGTH: 121
<212> TYPE: PRT
<213> ORGANISM: Artificial Sequence
<220> FEATURE:
<223> OTHER INFORMATION: 3rd_0.5_2_2A

<400> SEQUENCE: 57

Gln Val Gln Leu Val Gln Ser Gly Ala Glu Val Lys Lys Pro Gly Ser
1               5                   10                  15

Ser Val Lys Val Ser Cys Thr Ser Ser Glu Leu Leu Phe Pro Phe Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gln Ser Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Leu Pro Gly Gly Val Phe Asp His Trp Gly
            100                 105                 110

Gln Gly Thr Leu Val Thr Val Ser Ser
        115                 120

<210> SEQ ID NO 58
<211> LENGTH: 121
<212> TYPE: PRT
<213> ORGANISM: Artificial Sequence
<220> FEATURE:
<223> OTHER INFORMATION: 1101-181

<400> SEQUENCE: 58

Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Pro Met Phe
```

```
                    20                  25                  30

Ala Ile Ser Trp Val Arg Gln Ala Pro Gly Gln Gly Leu Glu Trp Leu
            35                  40                  45

Gly Gly Ile Ser Pro Met Phe Thr Met Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Leu Pro Ser Tyr Val Phe Asp His Trp Gly
            100                 105                 110

Gln Gly Thr Leu Val Thr Val Ser Ser
        115                 120

<210> SEQ ID NO 59
<211> LENGTH: 121
<212> TYPE: PRT
<213> ORGANISM: Artificial Sequence
<220> FEATURE:
<223> OTHER INFORMATION: H123#425

<400> SEQUENCE: 59

Gln Val Gln Leu Val Gln Ser Gly Ala Glu Val Lys Lys Pro Gly Ser
1               5                   10                  15

Ser Val Lys Val Ser Cys Thr Ser Ser Glu Val Leu Phe Pro Phe Phe
            20                  25                  30

Ala Ile Ser Trp Val Arg Gln Ala Pro Gly Gln Gly Leu Glu Trp Leu
            35                  40                  45

Gly Gly Ile Ser Pro Met Phe Gln Arg Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Ala Pro Ser His Val Phe Asp His Trp Gly
            100                 105                 110

Gln Gly Thr Leu Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: 3rd_1-4-B-02

<400> SEQUENCE: 60

Gln Val Gln Leu Val Gln Ser Gly Ala Glu Val Lys Lys Pro Gly Ser
1               5                   10                  15

Ser Val Lys Val Ser Cys Thr Ser Ser Glu Leu Met Phe Pro Tyr Phe
            20                  25                  30

Ala Ile Ser Trp Val Arg Gln Ala Pro Gly Gln Gly Leu Glu Trp Leu
            35                  40                  45

Gly Gly Ile Ser Pro Met Phe Asn Gln Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80
```

Met Asp Leu Arg Ser Leu Arg Ser Glu Asp Thr Ala Val Tyr Tyr Cys
                85                  90                  95

Ala Arg Ser Pro Ser Tyr Lys Pro Ile Gly Val Phe Asp His Trp Gly
            100                 105                 110

Gln Gly Thr Leu Val Thr Val Ser Ser
        115                 120

<210> SEQ ID NO 61
<211> LENGTH: 121
<212> TYPE: PRT
<213> ORGANISM: Artificial Sequence
<220> FEATURE:
<223> OTHER INFORMATION: 1101-150

<400> SEQUENCE: 61

Gln Val Gln Leu Val Gln Ser Gly Ala Glu Val Lys Lys Pro Gly Ser
1               5                   10                  15

Ser Val Lys Val Ser Cys Thr Ser Ser Glu Leu Phe Phe Pro Tyr Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Ser Leu Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Arg Pro Ser His Val Phe Asp His Trp Gly
            100                 105                 110

Gln Gly Thr Leu Val Thr Val Ser Ser
        115                 120

<210> SEQ ID NO 62
<211> LENGTH: 121
<212> TYPE: PRT
<213> ORGANISM: Artificial Sequence
<220> FEATURE:
<223> OTHER INFORMATION: 1026B52

<400> SEQUENCE: 62

Gln Val Gln Leu Val Gln Ser Gly Ala Glu Val Lys Lys Pro Gly Ser
1               5                   10                  15

Ser Val Lys Val Ser Cys Thr Ser Ser Glu Leu Phe Phe Pro Tyr Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Ser Leu Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Arg Pro Ser His Val Phe Asp His Trp Gly
            100                 105                 110

Gln Gly Thr Leu Val Thr Val Ser Ser
        115                 120

<210> SEQ ID NO 63
<211> LENGTH: 121
<212> TYPE: PRT
<213> ORGANISM: Artificial Sequence
<220> FEATURE:
<223> OTHER INFORMATION: 1026B77

<400> SEQUENCE: 63

Gln Val Gln Leu Val Gln Ser Gly Ala Glu Val Lys Lys Pro Gly Ser
1               5                   10                  15

Ser Val Lys Val Ser Cys Thr Ser Ser Glu Met Leu Phe Pro Tyr Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Ala Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Arg Pro Ser Gly Val Phe Asp His Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: 1101-170

<400> SEQUENCE: 64

Gln Val Gln Leu Val Gln Ser Gly Ala Glu Val Lys Lys Pro Gly Ser
1               5                   10                  15

Ser Val Lys Val Ser Cys Thr Ser Ser Glu Leu Gly Phe Pro Tyr Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Asp Phe Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Leu Pro Gly Ala Val Phe Asp His Trp Gly
            100                 105                 110

Gln Gly Thr Leu Val Thr Val Ser Ser
        115                 120

<210> SEQ ID NO 65
<211> LENGTH: 120
<212> TYPE: PRT
<213> ORGANISM: Artificial Sequence
<220> FEATURE:
<223> OTHER INFORMATION: F10 template

<400> SEQUENCE: 65

Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Thr Cys Val Phe Asp
                100                 105                 110

His Trp Gly Gln Gly Thr Leu Val
            115                 120

<210> SEQ ID NO 66
<211> LENGTH: 121
<212> TYPE: PRT
<213> ORGANISM: Artificial Sequence
<220> FEATURE:
<223> OTHER INFORMATION: 1026R66

<400> SEQUENCE: 66

Gln Val Gln Leu Val Gln Ser Gly Ala Glu Val Lys Lys Pro Gly Ser
1               5                   10                  15

Ser Val Lys Val Ser Cys Thr Ser Ser Glu Phe Met Phe Pro Tyr Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Glu Leu Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Val Pro Ser Gly Val Phe Asp His Trp Gly
                100                 105                 110

Gln Gly Thr Leu Val Thr Val Ser Ser
            115                 120

<210> SEQ ID NO 67
<211> LENGTH: 121
<212> TYPE: PRT
<213> ORGANISM: Artificial Sequence
<220> FEATURE:
<223> OTHER INFORMATION: 3rd_0.5-4-09H

<400> SEQUENCE: 67

Gln Val Gln Leu Val Gln Ser Gly Ala Glu Val Lys Lys Pro Gly Ser
1               5                   10                  15

Ser Val Lys Val Ser Cys Thr Ser Ser Glu Leu Val Phe Pro Leu Phe
            20                  25                  30

Ala Ile Ser Trp Val Arg Gln Ala Pro Gly Gln Gly Leu Glu Trp Leu
        35                  40                  45

```
Gly Gly Ile Ser Pro Met Phe Asn Lys Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Thr Tyr Leu Pro Arg His Val Phe Asp His Trp Gly
                100                 105                 110

Gln Gly Thr Leu Val Thr Val Ser Ser
                115                 120

<210> SEQ ID NO 68
<211> LENGTH: 121
<212> TYPE: PRT
<213> ORGANISM: Artificial Sequence
<220> FEATURE:
<223> OTHER INFORMATION: 3rd_0.5-2-2A

<400> SEQUENCE: 68

Gln Val Gln Leu Val Gln Ser Gly Ala Glu Val Lys Lys Pro Gly Ser
1               5                   10                  15

Ser Val Lys Val Ser Cys Thr Ser Ser Glu Leu Leu Phe Pro Phe Phe
                20                  25                  30

Ala Ile Ser Trp Val Arg Gln Ala Pro Gly Gln Gly Leu Glu Trp Leu
            35                  40                  45

Gly Gly Ile Ser Pro Met Phe Gln Ser Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Leu Pro Gly Gly Val Phe Asp His Trp Gly
                100                 105                 110

Gln Gly Thr Leu Val Thr Val Ser Ser
                115                 120

<210> SEQ ID NO 69
<211> LENGTH: 6
<212> TYPE: PRT
<213> ORGANISM: Artificial Sequence
<220> FEATURE:
<223> OTHER INFORMATION: consensus sequence-1

<400> SEQUENCE: 69

Ser Pro Met Phe Asn Gln
1               5

<210> SEQ ID NO 70
<211> LENGTH: 6
<212> TYPE: PRT
<213> ORGANISM: Artificial Sequence
<220> FEATURE:
<223> OTHER INFORMATION: consensus sequence-2

<400> SEQUENCE: 70

Ser Pro Leu Phe Asn Gln
1               5

<210> SEQ ID NO 71
<211> LENGTH: 6
```

```
<212> TYPE: PRT
<213> ORGANISM: Artificial Sequence
<220> FEATURE:
<223> OTHER INFORMATION: F10 CDR-H2 sequence

<400> SEQUENCE: 71

Ser Pro Met Phe Gly Thr
1               5

<210> SEQ ID NO 72
<211> LENGTH: 4
<212> TYPE: PRT
<213> ORGANISM: Artificial Sequence
<220> FEATURE:
<223> OTHER INFORMATION: F10-CDRH123 CDR-H2

<400> SEQUENCE: 72

Ser Pro Met Phe
1

<210> SEQ ID NO 73
<211> LENGTH: 12
<212> TYPE: DNA
<213> ORGANISM: Artificial Sequence
<220> FEATURE:
<223> OTHER INFORMATION: codon for Stop-Stop-E-F

<400> SEQUENCE: 73
taataagaat tc                                                            12
```

PHAGE-DISPLAYED ANTIBODY LIBRARIES AND USES THEREOF

BACKGROUND OF THE INVENTION

1. Field of the Invention

The present disclosure in general relates to the field of antibody library. More particularly, the present disclosure relates to the phage-displayed single-chain variable fragment (scFv) library comprising a plurality of scFvs with binding affinity and specificity to an epitope of H1N1 influenza hemagglutinin.

2. Description of Related Art

A large portion of the stem-specific antibodies bind to the hemagglutinin (HA) of influenza virus through the VH domain originated from human IGHV1-69 germline gene with only a few somatic mutations. B-cell receptors encoded with the germline VH sequence in IgM form can be activated by HA and the affinity maturation of the precursor IgG requires only 2 mutations in the complementarity determining region H1 (CDR-H1) and 5 mutations in the framework region 3 (FR3) to restore activity of a fully matured broadly neutralizing antibody (bnAb). Phage display selection of bnAbs specifically targeting the stem region of HA from a semi-synthetic antibody library overwhelmingly biased towards the germline IGHV1-69 sequence reveals that in addition to the two key germline-encoded residues in CDR-H2 (Ile53 and Phe54; antibody residue numbers are shown in Kabat number throughout this work) and Tyr98 in CDR-H3, a distinctive Ile52Ser mutation in the CDR-H2 and one additional mutation in the CDR-H1 can restore heterosubtypic neutralizing activity from a non-active precursor IgG encoded with germline IGHV1-69 sequence, suggesting that IGHV1-69-bnAbs can be efficiently matured from IGHV1-69-encoded B-cell receptors. Recent analysis of the developmental pathways of anti-stem IGHV1-69-bnAbs from a single donor confirms the key roles played by Phe54 and Tyr98 in the initial development of most IGHV1-69-bnAbs. But most strikingly, as few as 2~3 additional CDR-H1 and CDR-H2 mutations (Ser30Arg-Pro52AAla, or Thr28Pro-Ser30Ile-Ile53Val) in the IGHV1-69-encoded precursor IgG enable hetero-subtypic neutralizing activity, and moreover, additional favorable mutations can substitute the key roles of the aromatic side chains of Phe54 and Tyr98, suggesting that the affinity maturation pathways of the IGHV1-69-bnAbs could be redundant. All these results support the speculation that IGHV1-69 germline gene has been optimized by Darwinian evolution co-existed with the ubiquitous influenza virus infections in humans.

Structures of IGHV1-69-bnAbs in complex with HAs reveal a highly conserved antibody-antigen interaction interface. The antibody VH domain binds to the highly conserved patch on the stem region of HA mainly through the germline-encoded Phe54 in CDR-H2 in connection with the adjacent interaction involving Tyr98 in CDR-H3; CDR-H1 interacts with the stem region of HA through diverse configurations and the antibody VL domain does not make notable contact with the HA in the complex structures. CR6261 in complex with SC1918/H1 HA or Viet04/H5 HA interacts with two patches of epitope on HA: the membrane-distal patch composed of hydrophobic side chains from C-terminal end of helix A in HA2 and adjacent hydrophobic side chains from N- and C-terminal ends of HA1 interacts with Pro28 and Phe29 in CDR-H1 and Phe74 in FR3; the membrane-proximal patch composed of highly conserved Gly20, Trp21, Tyr22, and Ile/Val45 from HA2 with adjacent conserved His18 and His38 (conserved in group 1 HA) from HA1 interacts with IGHV1-69-encoded Ile53 and Phe54 in CDR-H2 and Tyr98 in CDR-H3 (HA residue numbers throughout this work are based on the numbering of the HA structure in 3GBN). The CDR-H1 adapts a non-canonical loop structure to make the side chain of Phe29 accessible for antigen binding even in the absence of the antigen. These interactions enable CR6261—a bnAb of the group 1 type A influenza viruses—neutralizing viral infection by inhibiting fusion of the viral membrane with that of the host cell. CR9114—a IGHV1-69-bnAb of both type A and B influenza viruses—recognizes the highly conserved membrane-proximal patch of the epitope on HA with CDR-H2 loop and Tyr98 in CDR-H3 in a complex structure mostly identical to that of CR6261, but the membrane-distal hydrophobic patch of the epitope interacts mostly with Phe74 in FR3 in the absence of the CR6261-like non-polar side chains in CDR-H1, which adapts the conventional type 1 canonical structure. F10—another IGHV1-69-bnAb of the group 1 type A influenza viruses—also recognizes the common IGHV1-69-bnAb epitope with similar CDR-H1~3 loop conformations: while the highly conserved membrane-proximal epitope patch is recognized with the paratope configuration similar to that of CR6261, the membrane-distal epitope patch is recognized with CDR-H1 loop adapting the type 1 canonical structure where the germline-encoded Phe29 is not accessible for antigen-binding and with the key aromatic side chain of Phe74 in FR3 replaced by small hydrophilic side chain of Ser. Unlike the aromatic interactions between the IGHV1-69 germline-encoded Phe54 with the highly conserved Trp21 of HA2 and His18 and His38 of HA1 common in all the three IGHV1-69-bnAbs, the interactions between the membrane-distal hydrophobic epitope patch and the bnAb CDR-H1/FR3 vary among the complex structures along with diverse CDR-H1 sequences and local conformations. The membrane-distal and membrane-proximal epitopes/paratopes in the complex structures of HA and F10 or CR6261 are published; the membrane-distal epitope and membrane-proximal epitope residue comparisons for 28627 HA sequences of Influenza A from all hosts and subtypes are shown in Table 1.

The atomic details of the IGHV1-69-bnAbs in complex with HA and the bnAbs' maturation pathways during vaccination or infection could lead to better designs of active immunotherapy to elicit universal bnAbs against influenza viruses, but other immunotherapeutic strategies based on antibody therapeutics and vectored immunoprophylaxis nevertheless require the bnAb amino acid sequences to be further optimized by exploring more expansive sequence space. Although by definition, bnAbs are able to recognize HA transcending subtypes of influenza virus, it is not expected that a single bnAb sequence could be optimally effective against diverse strains of HA because of the diverse sequences and local conformations of different HAs. It would be more reasonable to anticipate that optimal neutralizing antibodies for corresponding HA strains are to be attained from an antibody library constructed based on bnAb-HA recognition principles. These bnAb-HA recognitions are mediated either by heavy-chain CDR binding to the receptor-binding pocket on the head region of HA or by heavy-chain CDR binding to the stem region of HA, as described above. While both epitopes are vulnerable sites for broadly neutralizing antibodies, we focused only on the stem epitope of H1N1 HA in this work, because H1 is one of the major influenza virus subtypes and the H1 HA stem region sequences are highly conserved (Table 1). Hence, it is reasonable to anticipate that the antibody library developed herein could be applicable to some portion of H1 HA strains.

To elucidate the stem-specific antibody-HA recognition principles, we focused on first optimizing the CDR-H2 sequences of a bnAb against BS/07 H1 HA with a phage-displayed synthetic antibody library, aiming at exhaustively exploring the optimal interactions between the CDR-H2 loop and the highly conserved amino acid cluster on the membrane-proximal epitope of the HA stem. The sequence spaces of the CDR-H1 and CDR-H3 loops were then sequentially explored with additional phage-displayed library designs with the exhaustively optimized CDR residues fixed. The results suggested that the natural IGHV1-69-bnAbs have already been mostly optimized in the CDR-H2 sequences, especially in the CDR-H2 sequence of F10. The critical Tyr98 in CDR-H3 was well-conserved in the optimized CDR-H3 sequences, poised to augment the epitope-recognition by CDR-H2. By contrast, the essential sequence in the CDR-H1 is less well-defined, perhaps due to the flexibility of the loop conformation, ideally to accommodate the less conserved membrane-distal epitope on the HA stem. Together, IGHV1-69-bnAbs mainly recognize the highly conserved epitope patch in the stem region of HA with the largely globally optimized CDR-H2 and the somatic mutations in CDR-H1 can accommodate sequence variation in HA strains.

The findings enabled an antibody library design (named F10-CDRH123) aiming at generating specific neutralizing antibodies targeting the corresponding stem epitope on all strains of H1 HA. To test the antibody library design, we discovered more than 1000 antibody scFv leads from the phage-displayed F10-CDRH123 library panning against another H1 HA: CA/09 H1 HA. All these scFvs bound to the common IGHV1-69-bnAb epitope, and the maximum neutralizing potency was about 3~7 folds ($IC_{50}$) superior to that of F10 against CA/09 and BS/07 H1N1 influenza viruses. It is thus anticipated that corresponding neutralizing antibodies specific to the stem epitope of many H1 HAs could be developed from the phage-displayed F10-CDRH123 antibody library.

Given the fact that H1N1 influenza virus infection poses a major threat to the human population, there exists in the related art a need for a novel approach for producing an antibody so as to broadly inhibit the infection of different strains of H1N1 influenza virus.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The first aspect of the present disclosure pertains to a phage-displayed single-chain variable fragment (scFv) library, which comprises a plurality of scFvs that are expressed by a phage and exhibit binding affinity and specificity to a protein antigen.

According to one embodiment of the present disclosure, the scFv library comprises a plurality of scFvs, in which each of the plurality of scFvs comprises at least one polypeptide selected from the group consisting of, a first complementarity determining regionencoded by the nucleotide sequence of SEQ ID NO: 1, a second CDR encoded by the nucleotide sequence of SEQ ID NO: 2, and a third CDR encoded by the nucleotide sequence of SEQ ID NO: 3.

According to another embodiment of the present disclosure, the scFv library comprises a plurality of scFvs, in which each of the plurality of scFvs comprises, a first complementarity determining region of the heavy chain (CDR-H1) encoded by a first polynucleotide that comprises the nucleotide sequence of SEQ ID NO: 4, a second complementarity determining region of the heavy chain (CDR-H2) encoded by a second polynucleotide that comprises the nucleotide sequence of SEQ ID NO: 5, and a third complementarity determining region of the heavy chain (CDR-H3) encoded by a third polynucleotide that comprises the nucleotide sequence of SEQ ID NO: 6.

According to some embodiments of the present disclosure, the phage is M13 phage or T7 phage; preferably, the phage is M13 phage. In other embodiments, the protein antigen is a hemagglutinin of influenza virus.

The second aspect of the present disclosure is directed to a method for selecting one scFv from the scFv library described above. According to the embodiments of the present disclosure, the method comprises the steps of, (a) incubating the present phage-displayed scFv library with protein antigens, wherein the present phage-displayed scFv library comprises a plurality of phage-displayed scFvs;

(b) subjecting the product of step (a) to an acid treatment thereby producing a plurality of phage-displayed scFvs, which were respectively bound to the protein antigens before the acid treatment;

(c) subjecting the plurality of phage-displayed scFvs produced in the step (b) to an alkaline treatment; and (d) repeating at least one run of the steps (b) and (c), each time using the product of the step (c) in previous run as the phage library for incubating with the protein antigens, until the phage-displayed scFv exhibiting the highest binding affinity and specificity to the protein antigen is obtained.

According to the embodiment, the protein antigen is a hemagglutinin of influenza virus.

The third aspect of the present disclosure is directed to a phage-displayed scFv selected from the present scFv libraries.

In some embodiments, the selected phage-displayed scFv comprises at least one polypeptide selected from the group consisting of, a first CDR encoded by the nucleotide sequence of SEQ ID NO: 1, a second CDR encoded by the nucleotide sequence of SEQ ID NO: 2, and a third CDR encoded by the nucleotide sequence of SEQ ID NO: 3.

In other embodiments, the selected phage-displayed scFv comprises,

CDR-H1 encoded by a first polynucleotide that comprises the nucleotide sequence of SEQ ID NO: 4, CDR-H2 encoded by a second polynucleotide that comprises the nucleotide sequence of SEQ ID NO: 5, and CDR-H3 encoded by a third polynucleotide that comprises the nucleotide sequence of SEQ ID NO: 6.

The fourth aspect of the present disclosure pertains to a method of producing an antigen-specific recombinant antibody from the present phage-displayed scFv library described above. The method comprises the steps of, (1) incubating the present phage-displayed scFv library with protein antigens, wherein the present phage-displayed scFv library comprises a plurality of phage-displayed scFvs;

(2) selecting phages that express scFvs with binding affinity and specificity to the protein antigens;

(3) expressing the scFvs of the selected phages in the step (2) as soluble forms;

(4) selecting the soluble scFv of the step (3) that exhibits the highest binding affinity and specificity to the protein antigens;

(5) extracting a phagemid DNA that corresponds to the selected soluble scFv of the step (4);

(6) respectively amplifying a first nucleic acid sequence that encodes a first polypeptide comprising CDR-H1, CDR-H2, and CDR-H3, and a second nucleic acid sequence that encodes a second polypeptide comprising CDR-L1, CDR-L2, and CDR-L3 by PCR using the phagemid DNA of step (5) as a template;

(7) respectively inserting the first and second nucleic acid sequences into an expression vector that comprises a third and a fourth nucleic acid sequences, wherein the third nucleic acid sequence encodes a third polypeptide comprising the constant regions of a heavy chain of an immunoglobulin, and the fourth nucleic acid sequence encodes a fourth polypeptide comprising the constant regions of a light chain of the immunoglobulin; and (8) transfecting a host cell with the expression vector of step (7) comprising the first, second, third, and fourth nucleic acid sequences so as to produce the antigen-specific recombinant antibody.

According to one embodiment of the present disclosure, the first nucleic acid sequence is disposed at the upstream of the third nucleic acid sequence, and the second nucleic acid sequence is disposed at the upstream of the fourth nucleic acid sequence. According to another embodiment of the present disclosure, the immunoglobulin is selected from the group consisting of immunoglobulin G (IgG), immunoglobulin A (IgA), immunoglobulin D (IgD), immunoglobulin E (IgE), and immunoglobulin M (IgM). According to still another embodiment of the present disclosure, the host cell is a mammalian cell. In one specific example, the protein antigen is a hemagglutinin of influenza virus.

The fifth aspect of the present disclosure is directed to a method for the treatment of prophylaxis of influenza virus infection in a subject.

According to some embodiments, the method comprises the step of administering to the subject an effective amount of a recombinant antibody, in which the recombinant antibody comprises at least one polypeptide selected from the group consisting of, a first CDR encoded by the nucleotide sequence of SEQ ID NO: 1, a second CDR encoded by the nucleotide sequence of SEQ ID NO: 2, and a third CDR encoded by the nucleotide sequence of SEQ ID NO: 3.

According to other embodiments, the method comprises the step of administering to the subject an effective amount of a recombinant antibody, in which the recombinant antibody comprises, CDR-H1 encoded by a first polynucleotide that comprises the nucleotide sequence of SEQ ID NO: 4, CDR-H2 encoded by a second polynucleotide that comprises the nucleotide sequence of SEQ ID NO: 5, and CDR-H3 encoded by a third polynucleotide that comprises the nucleotide sequence of SEQ ID NO: 6.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

(FIG. 1A) The sequence LOGO was calculated from 95 CDR-H2 sequences, which were selected with the threshold of 0.3 in normalized binding affin the F10-CDRH123 phage-displayed antibody library.

FIG. 6. Designs and constructions of synthetic antibody libraries. The DNA (F10 template, SEQ ID NO: 7) and amino acid sequences (F10, SEQ ID NO: 65) of VH domain of the parent scFv are shown with Kabat numbering for amino acid residue positions, in which the FR1, FR2, FR3 and FR4 respectively define the framework region 1, framework region 2, framework region 3 and framework region 4 of VH domain of the parent scFv; and the CDRH1, CDRH2 and CDRH3 are respectively define the complementarity determining region H1, complementarity determining region H2 and complementarity determining region H3 of VH domain of the parent scFv. The primers for constructing each of the antibody libraries are shown below the VH amino acid sequence: for the F10-CDRH1 library, the Template_1 primer (SEQ ID NO: 8) was used to construct the template with stop codon (TAA) in the CDR-H1 region, and the library was diversified with the primer F10-CDRH1_1 (SEQ ID NO: 9) over the template; for the F10-CDRH2 library, the Template_2 primer (SEQ ID NO: 10) was used to construct the template, and the library was diversified with the primer F10-CDRH2_1 (SEQ ID NO: 11) over the template; for the F10-CDRH3 library, the Template_3 primer (SEQ ID NO: 12) was used to construct the template, and the library was diversified with the primer F10-CDRH3_1 (SEQ ID NO: 13) over the template; for the F10-CDRH123 library, the Template_1~3 primers (SEQ ID NOs: 8, 10 and 12) were used simultaneously to construct the template, and the library was diversified with the primers F10-CDRH123_1~3 (SEQ ID NOs: 14-16) simultaneously over the template. Primers different from their parent template sequences are underlined, where TAATAAGAATTC (SEQ ID NO: 73) encodes for Stop-Stop-EcoRI, and NNK for any of 20 amino acids.

DETAILED DESCRIPTION OF THE INVENTION

Figure 1A:
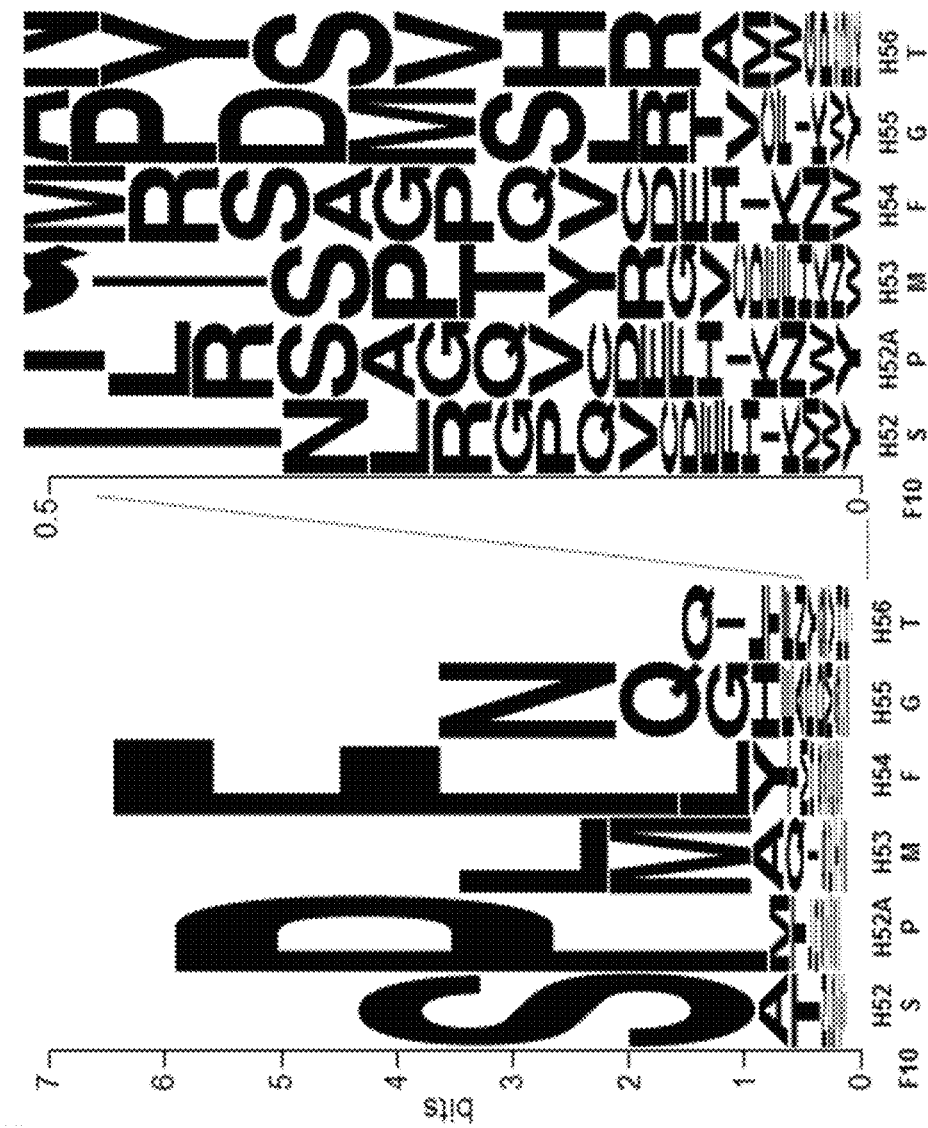
FIGS. 1A and 1B. Sequence LOGO of scFv variants with binding affinities and neutralizing potencies selected from the F10-CDRH2 phage-displayed antibody library.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleic acid sequence or a partial nucleic acid sequence encoding a protein that elicits an immune response, therefore encodes an "antigen" as that term is used herein. Furthermore, one skilled in the art will understand that an antigen needs not be encoded solely by a full length nucleic acid sequence of a gene; it can also be encoded by partial nucleic acid sequences of more than one gene and that these nucleic acid sequences are arranged in various combinations to elicit the desired immune response. Moreover, a skilled artisan will understand that an antigen needs not be encoded by a "gene" at all; it is readily apparent that an antigen can be synthesized or can be derived from a biological sample. Such a biological sample can include, but is not limited to, a tissue sample, a tumor sample, a cell or a biological fluid.

The term "antibody" is used in the broadest sense and specifically covers monoclonal antibodies (including full length monoclonal antibodies), polyclonal antibodies, multispecific antibodies (e.g., bi-specific antibodies), and antibody fragments so long as they exhibit the desired biological activity. "Antibody fragments" comprise a portion of a full length antibody, generally the antigen binding or variable region thereof. Examples of antibody fragments include Fab, Fab', F(ab')2, and Fv fragments; diabodies; linear antibodies;

single-chain variable fragment (scFv); single-chain antibody molecules; and multi-specific antibodies formed from antibody fragments.

The term "antibody library" refers to a collection of antibodies and/or antibody fragments displayed for screening and/or combination into full antibodies. The antibodies and/or antibody fragments may be displayed on a ribosome; on a phage; or on a cell surface, in particular a yeast cell surface.

As used herein, the term "single-chain variable fragment" or "scFv" is a fusion protein comprising the variable regions of the heavy (VH) and light chains (VL) of an immunoglobulin, in which the VH and VL are covalently linked to form a VH::VL heterodimer. The VH and VL are either joined directly or joined by a peptide-encoding linker, which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences.

The term "complementarity determining region" (CDR) used herein refers to the hypervariable region of an antibody molecule that forms a surface complementary to the 3-dimensional surface of a bound antigen. Proceeding from N-terminus to C-terminus, each antibody heavy and light chains respectively comprise three CDRs (CDR 1, CDR 2, and CDR3). A HLA-DR antigen-binding site, therefore, includes a total of six CDRs that comprise three CDRs from the variable region of a heavy chain and three CDRs from the variable region of a light chain. The amino acid residues of CDRs are in close contact with bound antigen, wherein the closest antigen contact is usually associated with the heavy chain CDR3.

In the present disclosure, the Kabat system (a well-known and widely used guide) is used to identify framework regions and CDRs of the invention-see *Sequences of Proteins of Immunological Interest*, E. Kabat et al., U.S. Department of Health and Human Services, 5$^{th}$ edition (1991). Identifying Kabat framework sequence is well-known and thus is a routine protocol. Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

The term "EC$_{50}$," as used herein, refers to the concentration of an antibody or an antigen-binding portion thereof, which induces a response, either in an in vitro or an in vivo assay, which is 50% of the maximal response, i.e., halfway between the maximal response and the baseline.

The term "IC$_{50}$", as used herein, refers to the concentration of an inhibitor (e.g. an antibody or antibody fragment) that inhibits a response in an assay half way between the maximal response and the baseline. It represents the antibody concentration that reduces a given response by 50%.

As used herein, the term "association rate constant (k$_{on}$)" refers to a value representing the intensity (degree) of association of the antibody with the target antigen thereof, which is determined based on the kinetics of the antigen-antibody reaction. The term "dissociation rate constant (k$_{off}$)" refers to a value representing the intensity (degree) of dissociation of the antibody from the target antigen thereof, which is determined based on the kinetics of the antigen-antibody reaction. The term "dissociation constant (K$_D$)" is calculated by dividing the "dissociation rate constant (k$_{off}$)" with the "association rate constant (k$_{on}$)." These constants are used as indexes representing the affinity of an antibody for its antigen and its activity neutralizing the antigen.

The term "phagemid" refers to a vector, which combines attributes of a bacteriophage and a plasmid. A bacteriophage is defined as any one of a number of viruses that infect bacteria.

"Nucleic acid sequence", "polynucleotide" or "nucleic acid" can be used interchangeably and are understood to mean, according to the present disclosure, either a double-stranded DNA, a single-stranded DNA or a product of transcription of said DNA (e.g., RNA molecule). It should also be understood that the present disclosure does not relate to genomic polynucleic acid sequences in their natural environment or natural state. The nucleic acid, polynucleotide, or nucleic acid sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

All degenerate nucleotide sequences are included within the scope of the invention as long as the peptide/polypeptide/protein (e.g., the present CDR) encoded by the nucleotide sequence maintains the desired activity or function. The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The terms "coding sequence" and "coding region" as used herein are interchangeable and refer to nucleotide sequences and nucleic acid sequences, including both RNA and DNA, that encode genetic information for the synthesis of an RNA, a protein, or any portion of an RNA or protein. Nucleotide sequences that are not naturally part of a particular organism's genome are referred to as "foreign nucleotide sequences", "heterologous nucleotide sequences", or "exogenous nucleotide sequences". "Heterologous proteins" are proteins encoded by foreign, heterologous or exogenous nucleotide sequences and therefore are often not naturally expressed in the cell. A nucleotide sequence that has been isolated and then reintroduced into the same type (e.g., same species) of organism is not considered to be a naturally occurring part of a particular organism's genome and is therefore considered exogenous or heterologous.

The term "similar" or "similarity" as used herein describes the relationship between different nucleic acid or amino acid sequences in which the sequences are related by partial sequence identity or sequence similarity at one or more blocks or regions within the sequence. Such similar amino acid residues may be either identical between different amino acid sequences, or represent conservative amino acid substitutions between different sequences.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the recombinant protein of the present disclosure), such as molar concentration, mass concentration, volume concentration, molality, mole fraction, mass fraction and mixing ratio. Persons having ordinary skills could calculate the human equivalent dose (HED) for the medicament (such as the present fusion protein) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

Unless otherwise indicated, a "therapeutically effective amount" of a recombinant protein is an amount sufficient to provide a therapeutic benefit in the treatment or management of a disease or condition, or to delay or minimize one or more symptoms associated with the disease or condition. A therapeutically effective amount of a recombinant protein is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, a "prophylactically effective amount" of a recombinant protein is an amount sufficient to prevent a disease or condition, or one or more symptoms associated with the disease or condition, or prevent its recurrence. A prophylactically effective amount of a recombinant protein means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "subject" refers to a mammal including the human species that is treatable with methods of the present invention. The term "subject" is intended to refer to both the male and female gender unless one gender is specifically indicated.

(i) Phage-Displayed scFv Library that Comprises Antibodies with at Least One Polypeptide Selected from the Group Consisting of CDRs Respectively Encoded by SEQ ID NOs: 1, 2, and 3

The first phage-displayed scFv library provided by the present disclosure comprises a plurality of scFvs that are expressed by a phage and exhibit binding affinity and specificity to a protein antigen. In the phage-displayed scFv library, each of the plurality of scFvs comprises at least one polypeptide selected from the group consisting of, a first CDR encoded by the nucleotide sequence of SEQ ID NO: 1, a second CDR encoded by the nucleotide sequence of SEQ ID NO: 2, and a third CDR encoded by the nucleotide sequence of SEQ ID NO: 3.

According to one embodiment of the present disclosure, the phage can be M13 phage or T7 phage; preferably, the phage is M13 phage.

According to another embodiment, the protein antigen is a hemagglutinin of influenza virus; for example, the protein antigen can be H1, H2, H3, H4, H5, H6, H7, H8, H9, H10, H11, H12, H13, H14, H15, H16, H17 or H18 hemagglutinin of influenza virus. In one working example, the protein antigen is H1 hemagglutinin of influenza virus; preferably, the H1 hemagglutinin is derived from BS/07 H1N1 strain (H1N1 A/Brisbane/59/2007). In another specific example, the protein antigen is H1 hemagglutinin derived from CA/09 H1N1 strain (H1N1 A/California/7/2009).

According to some embodiments, each of the plurality of scFvs comprised in the present phage-displayed scFv library can broadly bind to and neutralize different strains of influenza virus; for example, BS/07 H1N1 (H1N1 A/Brisbane/59/2007) or CA/09 H1N1 (H1N1 A/California/7/2009).

A phage-displayed scFv with high binding affinity and specificity to the protein antigen may be selected from the present phage-displayed scFv library. According to some embodiments, the method of selecting a phage-displayed scFv from the present phage-displayed scFv library comprises the steps of, (a) incubating the present phage-displayed scFv library with protein antigens, wherein the present phage-displayed scFv library comprises a plurality of phage-displayed scFvs;

(b) subjecting the product of step (a) to an acid treatment thereby producing a plurality of phage-displayed scFvs, which were respectively bound to the protein antigens before the acid treatment;

(c) subjecting the plurality of phage-displayed scFvs produced in the step (b) to an alkaline treatment; and (d) repeating at least one run of the steps (b) and (c), each time using the product of the step (c) in previous run as the phage library for incubating with the protein antigens, until the phage-displayed scFv exhibiting the highest binding affinity and specificity to the protein antigen is obtained.

In the step (a), the present phage-displayed scFv library, which comprises a plurality of phage-displayed scFvs, is incubated with protein antigens. Preferably, the protein antigens are immobilized on a supporting substrate, for example, resin, plate, slide, strip, or bead. According to one embodiment of the present disclosure, the protein antigens are immobilized on a strip. Non-limiting method used to immobilize the protein antigens to the supporting substrate includes, covalent immobilization (e.g., amine chemistry, thiol chemistry, carboxyl chemistry, epoxy chemistry, photoactive chemistry, site specific immobilization, diels-alder cycloaddition, click chemistry, and peptide ligation), bioaffinity immobilization (e.g., avidin-biotin system, his-tag system, DNA-directed immobilization, and protein A/protein G-mediated immobilization), and physical immobilization.

In the step (b), the product of the step (a) is subject to an acid treatment so as to separate the scFvs from their respective bound protein antigens. According to embodiments, the product of the step (a) is eluted with an elution buffer of pH 2.2 (e.g., a HCl/glycine solution), so as to disrupt the interaction between the protein antigen and the phage-displayed scFv.

Next, in the step (c), the thus produced phage-displayed scFvs in the step (b) are neutralized by use of an alkaline solution. According to embodiments of the present disclosure, the alkaline solution has a pH value of 9.0 (e.g., a Tris-based solution).

For the purpose of selecting an scFv exhibiting highest binding affinity and specificity to the protein antigen, the steps (b) and (c) are repeated for at least one run, each time using the alkaline-treated phage-displayed scFvs produced in the previous run as the starting phage library for incubating with the protein antigens, until the phage-displayed scFv exhibiting the highest binding affinity and specificity to the protein antigen is obtained.

Optionally, the alkaline-treated or neutralized phage-displayed scFvs produced in the step (c) may further be amplified in a host cell, for example, in *Escherichia coli* (*E. coli*) by infecting the host cell with the phage expressing the neutralized scFvs. Then, the amplified phage-displayed scFvs are incubated with the protein antigens, and the steps (b) and (c) are repeated, until the phage-displayed scFv exhibiting the highest binding affinity and specificity to the protein antigen is obtained.

According to the embodiments of the present disclosure, the protein antigen employed in the present method is a hemagglutinin of influenza virus; for example, the H1, H2, H3, H4, H5, H6, H7, H8, H9, H10, H11, H12, H13, H14, H15, H16, H17 or H18 hemagglutinin of influenza virus. In one working example, the protein antigen is H1 hemagglutinin of influenza virus, preferably, the H1 hemagglutinin derived from BS/07 H1N1 strain (H1N1 A/Brisbane/59/2007). In another example, the protein antigen is H1 hemagglutinin derived from CA/09 H1N1 strain (H1N1 A/California/7/2009).

According to one embodiment of the present disclosure, the selected phage-displayed scFv comprises at least one polypeptide selected from the group consisting of, a first CDR encoded by the nucleotide sequence of SEQ ID NO: 1, a second CDR encoded by the nucleotide sequence of SEQ ID NO: 2, and a third CDR encoded by the nucleotide sequence of SEQ ID NO: 3.

According to one embodiment, the selected phage-displayed scFv comprises a first CDR, which is encoded by the nucleotide sequence of SEQ ID NO: 1; in this embodiment, the first CDR comprises the CDR-H1 of the scFv, and the framework sequences respectively disposed at the N- and C-terminus of CDR-H1. According to another embodiment, the selected phage-displayed scFv comprises a second CDR, which is encoded by the nucleotide sequence of SEQ ID NO: 2; in this embodiment, the second CDR comprises the CDR-H2 of the scFv, and the framework sequences respectively disposed at the N- and C-terminus of CDR-H2. According to still another embodiment, the selected phage-displayed scFv comprises a third CDR, which is encoded by the nucleotide sequence of SEQ ID NO: 3; in this embodiment, the third CDR comprises part of the CDR-H3 of the scFv.

According to one embodiment, the selected phage-displayed scFv comprises the first and second CDRs, which are respectively encoded by the nucleotide sequences of SEQ ID NOs: 1 and 2. According to another embodiment, the selected phage-displayed scFv comprises the second and third CDRs, which are respectively encoded by the nucleotide sequences of SEQ ID NOs: 2 and 3. According to still another embodiment, the selected phage-displayed scFv comprises the first and third CDRs, which are respectively encoded by the nucleotide sequences of SEQ ID NOs: 1 and 3.

According to an alternative embodiment, the selected phage-displayed scFv comprises the first, second, and third CDRs, which are respectively encoded by the nucleotide sequences of SEQ ID NOs: 1, 2 and 3.

Further, a recombinant antibody having high binding affinity and specificity to the protein antigen may be produced from the present phage-displayed scFv library. The method for producing the recombinant antibody from the present phage-displayed scFv library comprises steps of, (1) incubating the present phage-displayed scFv library with protein antigens, wherein the present phage-displayed scFv library comprises a plurality of phage-displayed scFvs;

(2) selecting phages that express scFvs with binding affinity and specificity to the protein antigens;

(3) expressing the scFvs of the selected phages in the step (2) as soluble forms;

(4) selecting the soluble scFv of the step (3) that exhibits the highest binding affinity and specificity to the protein antigens, (5) extracting a phagemid DNA that corresponds to the selected soluble scFv of the step (4);

(6) respectively amplifying a first nucleic acid sequence that encodes a first polypeptide comprising CDR-H1, CDR-H2, and CDR-H3, and a second nucleic acid sequence that encodes a second polypeptide comprising CDR-L1, CDR-L2, and CDR-L3 by PCR using the phagemid DNA of step (5) as a template;

(7) respectively inserting the first and second nucleic acid sequences into an expression vector that comprises a third and a fourth nucleic acid sequences, wherein the third nucleic acid sequence encodes a third polypeptide comprising the constant regions of a heavy chain of an immunoglobulin, and the fourth nucleic acid sequence encodes a fourth polypeptide comprising the constant regions of a light chain of the immunoglobulin; and (8) transfecting a host cell with the expression vector of step (7) comprising the first, second, third, and fourth nucleic acid sequences so as to produce the antigen-specific recombinant antibody.

In the step (1), the present phage-displayed scFv library, which comprises a plurality of phage-displayed scFvs, is incubated with the protein antigens. With the similar selecting method performed in afore-mentioned step (a), the protein antigens are first immobilized on a supporting substrate (such as resin, plate, slide, strip, or bead) and mixed with the present phage-displayed scFv library. According to the embodiments of the present disclosure, the protein antigen is a hemagglutinin of influenza virus; for example, the H1, H2, H3, H4, H5, H6, H7, H8, H9, H10, H11, H12, H13, H14, H15, H16, H17 or H18 hemagglutinin of influenza virus. In one specific example, the protein antigen is H1 hemagglutinin of influenza virus. According to one preferred example, the H1 hemagglutinin is derived from BS/07 H1N1 (H1N1 A/Brisbane/59/2007) or CA/09 H1N1 (H1N1 A/California/7/2009).

In the step (2), the phages that express scFvs having binding affinity and specificity to the protein antigens are selected. In general, those phages can be selected in accordance with the selection method performed in afore-mentioned step (b) and (c). More specifically, the product of the step (1) (i.e., the phages that express scFvs having binding affinity and specificity to the protein antigens) is first subjected to an acid treatment (e.g., HCl/glycine solution of pH 2.2) followed by the treatment of alkaline solution (e.g., Tris-based solution of pH 9.0). According to one embodiment of the present disclosure, each of the scFvs expressed by the selected phages has a dissociation constant ($K_D$) of about $10^{-7}$-$10^{-9}$ M.

In the step (3), to exclude the possibility that the binding of protein antigen is mediated by the phage, rather than the scFv, the scFvs of the selected phages in the step (2) are respectively expressed as their secreted soluble forms. According to the embodiment of the present disclosure, the CDR regions of the scFv of the present phage-displayed scFv library are driven by a lactose operon (lac operon); as known by one skilled artisan, the lac operon would be induced by an isopropyl-thio-β-D-galactoside (IPTG) that then drives the expression of the down-stream genes. The produced scFvs are then secreted into the supernatant of culture medium and could be collected thereof.

In the step (4), the soluble scFvs produced in step (3) are selected by similar selection method performed in step (2), and then are mixed with the protein antigens pre-immobilized on a supporting substrate (such as resin, plate, slide, strip, or bead), which is then subject to the acid treatment so as to separate the scFvs from the protein antigens. The thus produced scFvs are further subject to alkaline treatment. According to one embodiment of the present disclosure, the selected soluble scFv exhibits the highest binding affinity and specificity to the protein antigen. In the embodiment, the selected soluble scFv has a $K_D$ of 80-100 pM. According to one specific example, the soluble scFv has a $K_D$ of 91 pM.

In the step (5), the phage that expresses the selected soluble scFv in the step (4) is lysed and the phagemid DNA is extracted thereof. The lysis and extraction could be performed via any conventional DNA extraction technique; for example, the phenol/chloroform assay, and detergent (e.g., sodium dodecyl sulfate, TWEEN-20 (polyoxyethylene (20) sorbitan monolaurate), NP-40 (nonyl phenoxypolyethoxylethanol), and TRITON X-100 (4-(1,1,3,3-Tetramethylbutyl)phenyl-polyethylene glycol))/acetic acid assay.

In the step (6), the extracted phagemid DNA in the step (5) serves as a template to respectively amplifying the first nucleic acid sequence that encodes the CDR-H1, CDR-H2, and CDR-H3, and the second nucleic acid sequence that encodes the CDR-L1, CDR-L2, and CDR-L3 by PCR.

In the step (7), the amplified first and second nucleic acid sequences are inserted into an expression vector, which comprises a third nucleic acid sequence encoding the constant regions of the heavy chain of an immunoglobulin, and a fourth nucleic acid sequence encoding the constant regions of the light chain of the immunoglobulin. According to one embodiment of the present disclosure, the first nucleic acid sequence is disposed at the upstream of the third nucleic acid sequence, and the second nucleic acid sequence is disposed at the upstream of the fourth nucleic acid sequence. As could be appreciated, the immunoglobulin can be any of IgG, IgA, IgD, IgE, and IgM. In one preferred embodiment of the present disclosure, the immunoglobulin is IgG; accordingly, the recombinant antibody produced by the present method comprises a four peptide chain: two identical heavy chains and two identical light chains linked by disulfide bonds and arranged in a Y-shape.

In the step (8), the expression vector constructed in step (7) is transfected into a host cell so as to produce the present recombinant antibody. The commonly used host cell is a mammalian cell, such as a HEK293 Freestyle cell. The transfection can be performed by any method familiar by one skilled artisan, including chemical-based method (e.g., calcium phosphate, liposome, and cationic polymer), non-chemical method (e.g., electroporation, cell squeezing, sonoporation, optical transfection, protoplast fusion, and hydrodynamic delivery), particle-based method (e.g. gene gun, magnetofection, and impalefection), and viral method (e.g., adenoviral vector, sindbis viral vector, and lentiviral vector). The thus produced recombinant antibody is secreted into the supernatant of the culture medium, and can be purified therefrom by any purification method familiar by any skilled person; for example, the purification can be achieved by affinity binding with protein A or protein G.

For the produced recombinant antibody is capable of binding and neutralizing different strains of influenza virus, it may provide a means to treat or prevent the influenza virus infection. Thus, the present disclosure also provides a method for the treatment or prophylaxis of influenza virus infection in a subject. According to the embodiments of the present disclosure, the method comprises the step of administering to the subject an effective amount (i.e., a therapeutically effective amount or a prophylactically effective amount) of a recombinant antibody, in which the recombinant antibody comprises at least one polypeptide selected from the group consisting of, a first CDR encoded by the nucleotide sequence of SEQ ID NO: 1, a second CDR encoded by the nucleotide sequence of SEQ ID NO: 2, and a third CDR encoded by the nucleotide sequence of SEQ ID NO: 3.

Specifically, the present recombinant antibody may comprise one CDR encoded by the nucleotide sequence of SEQ ID NO: 1, 2, or 3. Alternatively, the present recombinant antibody may comprise two CDRs respectively encoded by the nucleotide sequences of SEQ ID NOs: 1 and 2, 2 and 3, or 1 and 3. Alternatively, the present recombinant antibody may comprise three CDRs respectively encoded by the nucleotide sequences of SEQ ID NO: 1, 2 and 3.

In the embodiments of the present disclosure, the nucleotide sequences of SEQ ID NOs: 1-3 are represented by IUB (international unit of biochemistry) code, widely used by one of ordinary skill in the art, in which N designates as any nucleotide of A, T, C, or G; and K designates as G or T.

(ii) Phage-Displayed scFv Library that Comprises Antibodies with CDRs Respectively Encoded by SEQ ID NOs: 4, 5, and 6

Based on the observation that several amino acid residues in the CDR-H1, CDR-H2, and CDR-H3 regions mediate the interaction between the protein antigen and the present phage-displayed scFv, the present disclosure provides another phage-displayed scFv library. As the phage-displayed scFv library described in section (i), the second phage-displayed scFv library comprises a plurality of scFvs that are expressed by a phage and exhibit affinity and specificity to a protein antigen. According to the embodiments of the present disclosure, each of the plurality of scFvs comprises, CDR-H1 encoded by a first polynucleotide that comprises the nucleotide sequence of SEQ ID NO: 4, CDR-H2 encoded by a second polynucleotide that comprises the nucleotide sequence of SEQ ID NO: 5, and CDR-H3 encoded by a third polynucleotide that comprises the nucleotide sequence of SEQ ID NO: 6.

According to one embodiment of the present disclosure, the phage is M13 phage or T7 phage; preferably, the phage is M13 phage. According to another embodiment, the protein antigen is a hemagglutinin of influenza virus; for example, the H1, H2, H3, H4, H5, H6, H7, H8, H9, H10, H11, H12, H13, H14, H15, H16, H17 or H18 hemagglutinin of influenza virus. In one working example, the protein antigen is H1 hemagglutinin of influenza virus. According to one preferred example, the protein antigen is the H1 hemagglutinin derived from BS/07 H1N1 (H1N1 A/Brisbane/59/2007) or CA/09 H1N1 (H1N1 A/California/7/2009).

As the phage-displayed scFv library described in section (i), each of the plurality of scFvs comprised in the present phage-displayed scFv library can broadly bind to and neutralize different strains of influenza virus; non-limiting examples include BS/07 H1N1 (H1N1 A/Brisbane/59/2007) and CA/09 H1N1 (H1N1 A/California/7/2009).

According to the method described in section (i), a phage-displayed scFv with high binding affinity and specificity to the protein antigen (e.g., a hemagglutinin of influenza virus) may be selected from the present phage-displayed scFv library. The selected phage-displayed scFv comprises, CDR-H1 encoded by a first polynucleotide that comprises the nucleotide sequence of SEQ ID NO: 4, CDR-H2 encoded by a second polynucleotide that comprises the nucleotide sequence of SEQ ID NO: 5, and CDR-H3 encoded by a third polynucleotide that comprises the nucleotide sequence of SEQ ID NO: 6.

Further, according to the method described in section (i), a recombinant antibody may be produced from the present phage-displayed scFv library. The recombinant antibody can be expressed as IgG, IgA, IgD, IgE, and IgM, depending on the third and fourth nucleic acid sequences selected. In one example, the recombinant antibody is expressed as IgG.

According to other embodiments of the present disclosure, the $IC_{50}$ of the present recombinant antibody is about 230-270 ng/ml. The $EC_{50}$ of the present recombinant antibody is about 2.5-2.9 ng/ml. The $K_D$ of the present recombinant antibody to H1 hemagglutinin of influenza virus is about 91 pM.

For the recombinant antibody can efficiently bind to and neutralize different strains of influenza virus, the present disclosure further provides a method for the treatment or prophylaxis of influenza virus infection in a subject. The method comprises the step of administering to the subject an effective amount (i.e., a therapeutically effective amount or a prophylactically effective amount) of a recombinant antibody, in which the recombinant antibody comprises, CDR-H1 encoded by a first polynucleotide that comprises the nucleotide sequence of SEQ ID NO: 4, CDR-H2 encoded by a second polynucleotide that comprises the nucleotide sequence of SEQ ID NO: 5, and CDR-H3 encoded by a third polynucleotide that comprises the nucleotide sequence of SEQ ID NO: 6.

In the embodiments of the present disclosure, the nucleotide sequences of SEQ ID NOs: 4-6 are represented by IUB (international unit of biochemistry) code, widely used by one of ordinary skill in the art, in which N designates as any nucleotide of A, T, C, or G; and K designates as G or T.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Some relevant contents of the present invention have been published in *Scientific Reports* (Chao-Ping Tung et al.; 2015, 5: 15053; Discovering neutralizing antibodies targeting the stem epitope of H1N1 influenza hemagglutinin with synthetic phage-displayed antibody libraries). The entirety of the publication is incorporated herein by reference.

Materials and Methods

Cell Line and Viruses

Madin-Darby canine kidney (MDCK) epithelial cell line was cultured in Minimum Essential Medium Eagle (MEM) medium supplied with non-essential amino acids (NEAA), 2 mM L-glutamine, and 10% fetal bovine serum (FBS) in a 5% $CO_2$ humidified atmosphere incubator at 37° C. Influenza A viruses BS/07 H1N1 (A/Brisbane/59/2007) and CA/09 H1N1 (a recombinant virus NYMC X-181, HA from A/California/07/2009), supplied from Taiwan's CDC, were used in this study. Viruses' stocks were propagated in 10-day-old embryonic eggs' allantoic cavities, concentrated and resuspended in PBS. $TCID_{50}$ (50% tissue culture infectious dose) was used to determine virus titer in MDCK cells.

Phage-Displayed Synthetic Antibody Library Construction

The parent F10 template comprising the nucleotide sequence of SEQ ID NO: 7 served as a template to construct the present phage-displayed scFv libraries, including CDR-H1 library, CDR-H2 library, CDR-H3 library, and CDR-H123 library, by oligonucleotide directed mutagenesis (also known as site-specific mutagenesis or site-directed mutagenesis) with specified primers.

CDR-H1 Library

For the construction of CDR-H1 library, a Template_1 primer having the nucleotide sequence of SEQ ID NO: 8 was used to mutate the CDR-H1 region of the parent F10 template. The mutated DNA fragment had two stop codons (TAA) in the CDR-H1 region. Then, the mutated DNA fragment was diversified with the primer F10-CDRH1_1 having the nucleotide sequence of SEQ ID NO: 9. The diversified DNA fragments were constructed into to the phagemid pcantab5E by Kunkel method so as to produce the CDR-H1 library.

CDR-H2 Library

To construct the CDR-H2 library, a Template_2 primer having the nucleotide sequence of SEQ ID NO: 10 was used to mutate the CDR-H2 region of the parent F10 template. Then, the mutated DNA fragment was diversified with the primer F10-CDRH2_1 having the nucleotide sequence of SEQ ID NO: 11. The diversified DNA fragments were constructed into to the phagemid pCantab5E by Kunkel method so as to produce the CDR-H2 library.

CDR-H3 Library

To construct the CDR-H3 library, a Template_3 primer having the nucleotide sequence of SEQ ID NO: 12 was used to mutate the CDR-H3 region of the parent F10 template. Then, the mutated DNA fragment was diversified with the primer F10-CDRH3_1 having the nucleotide sequence of SEQ ID NO: 13. The diversified DNA fragments were constructed into to the phagemid pCantab5E by Kunkel method so as to produce the CDR-H3 library.

CDR-H123 Library

For the construction of CDR-H123 library, the primers Template_1, Template_2 and Template_3 respectively having the nucleotide sequences of SEQ ID NOs: 8, 10 and 12 were used to mutate the CDR-H1, CDR-H2 and CDR-H3 regions of the parent F10 template. Next, the mutated DNA fragments were diversified with the primers F10-CDRH123_1, F10-CDRH123_2 and F10-CDRH123_3 simultaneously having the nucleotide sequences of SEQ ID NOs: 14-16. The diversified DNA fragments were constructed into to the phagemid pCantab5E by Kunkel method so as to produce the CDR-H123 library.

E. coli (strain ER2738) harboring the phagemid libraries was cultured to produce recombinant M13 phages expressing the antibody scFv libraries as pIII-fusion proteins on the phage particles, which were rescued with helper phage M13KO7. The recombinant phages expressing the scFv libraries were precipitated by polyethylene glycol/NaCl (PEG/NaCl) and then resuspended in phosphate buffered saline (PBS) for the following selection-amplification cycles. The quality of the phage-displayed scFv libraries were assessed by tittering the colony forming units per mL (CFU/mL) and by random sequencing of the single E. coli colonies harboring the phagemids. The tittering results suggested that all the synthetic phage-display libraries had complexity >$10^9$ and the sequence LOGOs for the library variants (data not shown) indicated that the expression of the variable sequences were not substantially biased by phage library preparation.

Phage Display Panning for Anti-HA Antibodies

The 8-well strip coated with HA proteins (1 µg/100 µL PBS per well) was used for panning anti-HA antibodies based on the protocol described previously. In brief, the wells were coated with HA by shaking the coating solution in the wells for 2 hrs at room temperature. The HA-coated wells were then treated with blocking buffer (5% skim milk in PBST (phosphate buffered saline with 0.1% TWEEN-20 (polyoxyethylene (20) sorbitan monolaurate)) for 1 hr at room temperature. Recombinant phages in the blocking buffer diluted to $10^{12}$ CFU/mL were added to the HA-coated wells for 1 hr with gentle shaking. The wells were then washed vigorously 10 times with PBST, followed by 6 times with PBS to remove nonspecific binding phages. The bound phages were eluted (0.1 M HCl/glycine (pH 2.2) for 10 min), and the elution solution was neutralized immediately by 2 M Tris-base buffer (pH 9.0). E. coli strain ER2738 ($OD_{600}$=~0.6) was used for phage infection at 37° C. for 30 min; non-infected E. coli was eliminated by treating with ampicillin for 30 min. After ampicillin treatment, helper phage M13KO7 was added for another 1 hr incubation. Selected phages in the E. coli culture were amplified with vigorously shaking overnight at 37° C. in the presence of kanamycin. The amplified phages were precipitated in PEG/NaCl, and then resuspended in PBS for the next selection-amplification cycles.

Binding and Concentration Characterization of Phage-Free Soluble scFv in Culture Supernatant E. coli strain ER2738 grown in the mid-log phase in 2YT broth (16 g/L tryptone, 10 g/L yeast extract, 5 g/L NaCl, pH 7.0) in deep well plates was infected with single-clonal phages harboring a selected scFv gene in their phagemids. After one hour incubation at 37° C. with shaking, ampicillin was added to the final concentration of 100 µg/mL. IPTG was added to final concentration of 1 µg/mL until broth $OD_{600}$ reach 1.0-1.2. The plates were incubated at 37° C. overnight with rigorously shaking. After the spin-down of the bacteria in the cell culture solution, the supernatant with phage-free soluble scFv (expressed with E-tag fused to the C-terminus) was filtrated by the filter plate with 0.45 µm membrane to remove bacteria from contaminating the following micro-neutralization assays.

For soluble scFv binding test, ELISA assay was carried out following the previous methods with some modifications. In brief, 96-well microtiter plate was coated with BS/07 or CA/09 H1 HA (0.5 µg/100 µL PBS per well) for 2 hrs with shaking at room temperature. After treated with 300 µL of blocking buffer for 1 hr, 50 µL of secreted scFv in the filtered supernatant was mixed with fresh 50 µL of blocking buffer and then added to the coated microtiter plate for another 1 hr under gently shaking. Goat anti-E-tag antibody (conjugated with HRP, 1:4000) was added to the microtiter plate for 1 hr. TMB peroxidase substrate (100 µL per well) was added to the wells and the absorbance at 450 nm was measured after reactions were stopped by adding 1N HCl (100 µL per well). Each scFv in its respective filtered supernatant was assayed in triplicate.

The concentration of the scFv in its respective filtered supernatant was measured with the dot-blot procedure: PVDF membrane rinsed with methanol and equilibrated with PBS buffer was immobilized. Samples of secreted scFv in culture broth were added into each well. Serially diluted F10-E-tag scFv of known concentration was also loaded to establish standard controls. The membranes were blocked with 5% skim milk in PBST, and then developed with anti E-tag antibody (conjugated with HRP) followed by chromogenic TMB peroxidase substrate treatment.

Normalized binding affinities of scFvs were the ELISA readings divided by concentration quantification, and normalized with that of the F10 control, i.e., $(E_S/Q_S)/(E_{F10}/Q_{F10})$, where $E_S$ and $E_{F10}$ were ELISA readings of the sample and the F10 controls respectively, and $Q_S$ and $Q_{F10}$ were concentration quantification of the sample and the F10 control respectively. The averaged values and the standard deviations of the normalized binding affinities were calculated with multiple measurements.

Micro-Neutralization Assay for Influenza Virus Infection

MDCK cells ($3\times10^4$ cell per well) were seeded in 96-well plates and cultured for 16 hrs to confluency. Filtrated scFvs were mixed with 100 $TCID_{50}$ freshly diluted viral solution for 30 min at 37° C. Virus-scFv mixtures were then added to infect PBS-washed MDCK cells for 1 hr at 37° C. After absorption, virus-scFv mixtures were removed and MDCK cells were washed with PBS twice. Infected MDCK cells were cultured and fixed with methanol-acetone (1:1 (v/v)) 24 hrs post-infection. After fixation, MDCK cells were treated with 0.5% TRITON X-100 in PBS for 5 min, and then with blocking buffer for 1 hr. The mouse anti-influenza A viral nucleoprotein IgG antibody (1:2000) was used for detection of viral nucleoprotein production with goat anti-mouse antibody-HRP and TMB peroxidase substrate. Each filtrated scFv was assayed in quadruplicates.

The ELISA readings of virus-only control was set as 0%, and that of negative control (no virus and no scFv) was set as 100%. The reduction of virus infection due to scFv addition was calculated as neutralization percentage. Normalized neutralizing potency was the neutralization percentage divided by concentration quantification, and normalized with that of F10, i.e., $(Ns/Q_S)/(N_{F10}/Q_{F10})$, where Ns and $N_{F10}$ were the neutralization percentage of the sample scFv and the F10 scFv control respectively, and $Q_S$ and $Q_{F10}$ were the concentration quantification of the sample scFv and the F10 scFv control respectively. The averaged values and the standard deviations of the normalized neutralizing potencies were calculated with multiple measurements.

Sequence LOGO

The size $R_{ji}$ (in half-bit unit) for amino acid type i at position j in the consensus sequence LOGOs were calculated with the equation:

$$d_{ji} = q_{ji} I_j \quad (1)$$

$$I_j = \sum_{i=1}^{20} 2q_{ji} \log_2 \frac{q_{ji}}{p_i}$$

$$q_{ji} = \frac{C_{ji} + \sqrt{M_j}\, p_i}{(M_j + \sqrt{M_j})}.$$

$C_{ji}$ is the count for amino acid i at position j in $M_j$ count of HA-binding CDR sequences containing position j; pi is the background probability for amino acid i encoded in the NNK degenerate codon; the square root of $M_j$ in the equation is the pseudo count to prevent singularity when $C_{ji}$ equals to zero. Equation (1) is modified after the original formulation.

Position Specific Score Matrix (PSSM) and Scoring of Germline Sequences

The position specific score matrix (PSSM) $W_{ji}$, are expressed in half-bite units calculated with the Bayesian prediction pseudo-count method:

$$W_{ji} = 2 \log_2 \left[ \frac{C_{ji} + \sqrt{M}\, p_i}{(M + \sqrt{M})p_i} \right] \quad (2)$$

where $W_{ji}$ is the preference for amino acid i at position j in the CDR of the antibody; $C_{ji}$ is the count for amino acid i at position j in M count of HA-binding CDR sequences containing position j; $p_i$ is the background probability for amino acid i encoded in the NNK degenerate codon; the square root of M in the equation is the pseudo count to prevent singularity when CO; equals to zero.

The matching score of a germline CDR sequence to a set of M antibody CDR sequences was calculated with the PSSM described in the previous paragraph. CDR H1 and CDR H2 of each germline sequence were first identified with the previous published method; the matching score is the sum of W; (Equation (2)) over the entire CDR sequence, where i is the germline amino acid type at the corresponding position j in the CDR sequence.

HA Sequence Analysis

All full length HA sequences were downloaded from Influenza Research database (as of December 2014). A total of 28627 sequences of Influenza A from all hosts and subtypes were collected for identifying amino acid conservations of membrane-proximal epitopes and membrane-distal epitopes. The HA sequences were aligned within each subtype. The statistic details are summarized in Table 1.

Expression and Purification of Hemagglutinin (HA) in Insect Cells cDNAs corresponding to residues 18-528 of the ectodomain of the hemagglutinin (HA) from A/Brisbane/59/2007 (H1N1; Accession No. ACA28844.1, BS/07 H1 HA) and residues 18-529 from the A/California/07/2009 (H1N1; Accession No. ACP41953.1, CA/09 H1 HA) were codon-optimized for eukaryotic cell expression and fused to an N-terminal gp67 signal peptide (MLLVNQSHQGF-NKEHTSKMVSAIVLYVLLAAAAHSAFAADLAS, SEQ ID NO: 17) and to a C-terminal thrombin cutting site, trimerization domain and $His_6$-tag (ASLVPRGSPGSGYI-PEAPRDGQAYVRKDGEWVLLSTFLGHHHHHH, SEQ ID NO: 18) by PCR as described previously. These HA expression cassettes were inserted into pFastBac-1, a baculoviral transfer vector. HA protein was produced by infecting suspension cultures of Sf9 cells ($3 \times 10^6$ cell/mL) with recombinant baculovirus at an MOI of 5 and incubated at 26° C. shaking at 110 rpm for 72 hrs. The cultures were clarified by two rounds of centrifugation (1,000×g and 12,000×g for 30 min, 4° C.). The supernatants containing HA was dialyzed by PBS, pH 7.2 for overnight at 4° C. Before $Ni^{2+}$-charged IMAC column binding, the dialyzed solution was filtered by 0.8 µm pore size filter. The HA was purified by $Ni^{2+}$-charged IMAC column chromatography by gradient from 40 mM to 500 mM imidazole in TS solution (Tris-HCl, 10 mM, NaCl 50 mM, pH 8.0). The fractions containing HA were introduced to the column chromatography and eluted by gradient from 40 mM to 1000 mM NaCl in Tris-HCl, 10 mM, pH 8.0. The fractions containing HA were concentrated and introduced to the column for size exclusion chromatography with TS solution. The fractions containing HA were collected and stored in 4° C. or −80° C. with proteinase inhibitor cocktail.

Expression and Purification of scFv

The expression and purification of the scFv followed the method described previously with minor modifications. In brief, the scFv coding region was subcloned into pET-32 expression vector encoding thioredoxin as a fusion protein N-terminal to the scFv. The fusion protein contains a hexa-His tag followed by a TEV protease cutting site between the thioredoxin and the scFv, which is followed by an oligo-peptide (GLNDIFEAQKIEWHE, SEQ ID NO: 19) appending to the C-terminus of the scFv for in vivo biotinylation. The scFv gene derived from phage panning was subcloned into the expression vector via the SfiI and NotI cutting sites encompassing the scFv coding region. E. coli transformed with scFv expression vector was grown in 2× YT medium (Tryptone 16 g/L, Yeast extract 10 g/L, NaCl 5 g/L) with ampicillin (200 µg/L), tetracycline (12.5 µg/L) and chloramphenicol (37.5 µg/L) at 37° C. until $OD_{600}$ reached 1.0, and was then incubated at 16° C. for another 2 hours before adding 0.2 mM IPTG. After overnight protein expression and centrifugation, the cell pellets were resuspended in lysis buffer (Tris-HCl, 50 mM, pH 8.0, 150 mM NaCl, 30 mM imidazole) and the suspended cells were then broken by MICROFLUIDIZER. The recombinant thioredoxin-scFv fusion protein was purified by nickel chelation chromatography with IMAC prepacked column charged by 0.1 M $NiSO_4$ solution. The fractions containing the fusion protein were collected and dialyzed by Tris-HCl, 50 mM, pH 7.5 (the theoretical pI of sc-dsFv was 5.82) overnight at 4° C. or desalted by a desalting column with the same buffer. The protein solution was then introduced to ion-exchanged chromatography. The fractions containing the thioredoxin-scFv fusion protein were collected and treated with $His_6$-tagged TEV protease ($A_{280}$ ratio 50:1) at 30° C. for at least 5 hr but not longer than 8 hr. The TEV-cleaved fragment containing $His_6$-tagged thioredoxin and the $His_6$-tagged TEV protease were removed by nickel chelation chromatography. The fractions containing scFv were further purified with a size-exclusion column in SEC buffer (Tris-HCl, 50 mM, pH 7.5, 400 mM NaCl, 10% glycerol). The soluble scFv protein was prepared with 95% purity. The purified sc-dsFv was stored at 4° C. for a least one week without affinity loss.

Construction and Expression of IgG

VH and VL DNA fragments were respectively amplified by PCR using the primers of SEQ ID NOs: 20-23. The amplified VH and VL DNA fragments were assembled into the plasmid for IgG1 expression with the pIgG expression system with cloning kit. IgGs were expressed by 293F cells. 293F cells were subcultured to a final $1-1.5 \times 10^6$ cells/mL in culture medium, and incubated for 2-4 hrs at 37° C. (8% $CO_2$, 110 rpm). Each IgG construction was transfected into 293F cells with PEI (polyetherimide)) according to supplier's protocol. Expressed IgG was collected from cell culture supernatant 7-9 days or until cell viability drops below 60% after transfection. PROTEIN A SEPHAROSE was reconstituted and packed as manufacture's instruction described. The 293F cell cultures were centrifuged and filtrated through 0.22 μm filter. The IgG was purified through protein A column, eluted with 0.2 M glycine/HCl buffer, pH 2.5, and neutralized with 1 M Tris buffer, pH 9.0.

Antibody-Antigen Interaction Affinity and Kinetics Measurements by Surface Plasmon Resonance BIACORE T200 instrument was used to determine the binding affinities and kinetic parameters for interactions between IgGs and HA protein. HA in 10 mM acetate buffer (pH 5.0) was immobilized on a CM5 sensor chip to a response unit (RU) of 1000 with an amine coupling kit. Association ($k_{on}$) and dissociation ($k_{off}$) constants of the interactions between IgGs and HA were measured in HBS-EP+ buffer with a flow rate of 30 μL/min. The sensor surface was regenerated with 50 mM HCl with 0.05% surfactant P20 (polyoxyethylene (20) sorbitan monolaurate), prior to a new IgG injection and the signals obtained were subtracted by that obtained from the reference channel that had not been coated with ligands. Binding kinetics was determined by global fitting to 1:1 binding model using the BIAevaluation software.

$IC_{50}$ Measurement

The half of maximal inhibitory concentration ($IC_{50}$) was determined to evaluate neutralization ability of IgG. MDCK cells were seeded in 96-well plates and cultured for 16 hrs to confluency. Virus stock was freshly diluted by infection buffer. Purified IgG diluted with PBS were mixed with 100 $TCID_{50}$ viral solution for neutralization. Virus-IgG mixtures were then added to infect PBS-washed MDCK cells. After absorption, virus-scFv mixtures were removed and MDCK cells were washed with PBS and cultured in fresh infection buffer, and fixed with methanol-acetone (1:1 (v/v)) 24 hrs post-infection. After fixation, MDCK cells were treated with 0.5% TRITON X-100 in PBS and then blocking buffer. Mouse anti-influenza A viral nucleoprotein IgG antibody and HRP conjugated goat anti-mouse antibody with TMB peroxidase substrate were used to monitor the virus propagation during antibody treatment. Each concentration of diluted IgG was assayed six replicates. The $IC_{50}$ (ng/mL) was calculated according to Stewart and Watson method.

Example 1 Global Search of the CDR-H2 Sequence of F10-Derived Binders Against a HA Revealed Sequence Preference Profiles Only Compatible with the IGHV1-69*01 Gene The F10 scFv (single chain variable fragment) was used as a model antibody molecule to exhaustively explore the sequence space of CDR-H2 for residues ranging from H52 to H56—the CDR-H2 region defined by Chothia. The aim was to explore globally optimal CDR-H2 sequences targeting the highly conserved membrane-proximal epitope on HA (Table 1). We used F10 scFv as the template because the VH-VL scFv of F10 was successfully expressed both as M13-phage displayed scFv and as phage-free soluble scFv in the supernatant of E. coli culture, although the expression of the phage-displayed scFv of CR6261 was known previously. The phage-displayed synthetic antibody library (F10-CDRH2) was constructed with the F10 template (FIG. 6), where the CDR-H2 region was diversified with degenerate codon NNK (N: A/G/T/C and K: G/T) to cover all 20 natural amino acid types. Oligonucleotide directed mutagenesis was used to construct the phage-displayed F10-CDRH2 library with complexity >$10^9$, which was comparable to the theoretical gene diversity ($32^6$) of the antibody library by design. Phage-displayed scFvs from the F10-CDRH2 library were selected with 3 rounds of selection-amplification phage display cycle against immobilized recombinant BS/07 H1 HA. The selected scFvs were then expressed as phage-free soluble scFv in the supernatant of the cell culture, which was tested for binding to the recombinant BS/07 H1 HA and with micro-neutralization assay on BS/07 H1N1 (H1N1 A/Brisbane/59/2007) and CA/09 H1N1 (H1N1 A/California/7/2009) viral infection to MDCK cells (Table 2 for representative variants).

TABLE 1

Amino acid conservations of membrane-proximal epitopes and membrane-distal epitopes from HA sequences of all subtypes of Influenza A viruses in the Influenza Research database

| | | | Membrane-distal epitopes | | | | | | Membrane-proximal epitopes | | | | | | |
| | | | HA1 | | | HA2 | | | HA1 | | HA2 | | | | | |
| | Subtype | Number | 40 | 42 | 292 | 49 | 52 | 56 | 18 | 38 | 19 | 20 | 21 | 22 | 23 | 41 | 45 |
|---|---|---|---|---|---|---|---|---|---|---|---|---|---|---|---|---|---|
| Group1 | H1 | 5935 | V/I | L | L | T/S | V | I | H | H | D | G | W | Y | G | T | I |
| | H2 | 510 | K/Q | I | L | T | V | I | H | H | D | G | W | Y | G | T | I/FV |
| | H5 | 3614 | Q | I | M/L | T | V | I | H | H | D | G | W | Y | G | T | I/V |
| | H6 | 1298 | V/I | L | L | T | V | I | H | H | D | G | W | Y | G | T | I/V |
| | H8 | 115 | M | L | K/R | T/S | V/I | V | Q | Q | D | G | W | Y | G | T | I |
| | H9 | 1525 | K | L | L | T | V | V/I | Q | H | A | G | W | Y | G | T | I/V |
| | H11 | 492 | V/I | L | R/K | T | V | V | L | S | N | G | W | Y | G | T | I/V |
| | H12 | 148 | E | L | K | Q | L | I | Q | Q | A | G | W | Y | G | T | I/M |
| | H13 | 82 | V/I | L | K/R | T | I | I | L | S | N | G | W | Y | G | T | I |
| | H16 | 40 | V/I | L | K/R | T | I | I | L | S | N | G | W | Y | G | T | I/L |
| | H17 | 3 | Q | I | L | T | V | I | Q | G | D | G | W | Y | G | T | V |
| Group2 | H3 | 11651 | T | L | K/R | N/T | L | I | H | N | D | G | W | Y | G | T | I |
| | H4 | 1217 | Q | L | K | N | L | I/V | H | T/A | D | G | W | Y | G | T | I |
| | H7 | 1404 | T | T | L | T | L | I | H | N | D/N | G | W | Y | G | T | I/V |
| | H10 | 570 | T | T | L | T | L | I/V | H | N | D | G | W | Y | G | T | I/V |

TABLE 1-continued

Amino acid conservations of membrane-proximal epitopes and membrane-distal epitopes from HA sequences of all subtypes of Influenza A viruses in the Influenza Research database

| | | Membrane-distal epitopes | | | | | | | Membrane-proximal epitopes | | | | | | |
|---|---|---|---|---|---|---|---|---|---|---|---|---|---|---|---|
| | | HA1 | | | HA2 | | | HA1 | | HA2 | | | | | |
| Subtype | Number | 40 | 42 | 292 | 49 | 52 | 56 | 18 | 38 | 19 | 20 | 21 | 22 | 23 | 41 | 45 |
| H14 | 10 | K | L | K | N | L | I/V | H | S | D | G | W | Y | G | T | I |
| H15 | 13 | T | T | L | T | L | I | H | N | D | G | W | Y | G | T | I |

Only amino acid types showing frequencies higher than 1% are shown. The most predominant amino acid types are shown first, followed by other minor amino acid types after slash. The bold character represents the amino acid type with frequency higher than 98%. The third column from left indicates the number of sequences in the Influenza Research database (as of December 2014) belonging to the specific subtype. The residue position numbering scheme (third row from top) follows the crystal structure of CR6261-HA complex (PDB ID: 3GBN.)

One critical condition in the phage-display selection/amplification cycles was to ensure that optimized scFv binders relevant to the stem-specific antibody-HA neutralization mechanism could be separated from the antigen with elution buffer for further amplification. The elution buffer at pH 2.2 (Methods) is sufficient to shift the electrostatic interactions involving real charges in the antibody-antigen interfaces by removing the charges on aspartic acids and glutamic acids and by adding real charges on histidines on the antibody-antigen complexes. As such, most of the bound scFvs on the immobilized antigens should be eluted from the solid substrate, although there is no assurance that all binders could be eluted under this elution condition. The F10 scFv-HA interactions at neutral pH (pH 8 to pH 6) are abolished at pH lower than 5, where most of the histidines in the antibody-antigen interface are charged, weakening the binding energetics due to real charge electrostatic interactions. This result suggests that the neutralizing potency of F10 does not require sustained binding to HA below pH 5, although it is known that stem-specific neutralizing antibodies bind to HA in the acidic environment of the endosome to prevent conformational change of the HA. Together, the elution condition was sufficient to select at least a portion of the scFvs with neutralizing potency against HA for further amplification, but the neutralizing capabilities of the selected scFvs needed to be determined experimentally to confirm the validity of the phage-display selection/amplification cycles during the optimization of the binding affinity and neutralizing potency of the scFvs from the phage-displayed antibody library.

The selected phage-displayed scFvs from the selection/amplification cycles were indeed capable of neutralizing the corresponding influenza viruses, but the binding affinity and the neutralizing potency of these selected scFvs were poorly correlated. While the maximal binding affinities of the selected scFv variants to HA were a few folds higher than that of F10 scFv, the neutralizing potencies of these scFv variants against both BS/07 and CA/09 H1N1 viruses were not clearly superior to that of F10 scFv. The binding affinities of 108 selected scFv variants from the F10-CDRH2 library had no clear linear correlation ($r^2<0.01$) with their neutralizing potencies against the corresponding influenza virus (data not shown). Total 108 scFv variants are analyzed. The sequences and the binding/neutralization data of representative scFv variants are summarized in Table 2. These results suggested that the F10 CDR-H2 sequence had been mostly optimized for neutralizing both of the H1N1 viruses.

TABLE 2

Data for the representative scFv variants selected from the F10-CDRH2 library

| scFv | SEQ IDNO | concentration (µg/ml) | normalized neutralizing potency against BS/07 H1N1 | normalized neutralizing potency against CA/09 H1N1 | normalized binding affinity to BS/07 H1N1 |
|---|---|---|---|---|---|
| F10 | 65 | 1.347 ± 0.109 | 1.000 | 1.000 | 1.000 |
| H2-143 | 24 | 0.061 ± 0.001 | 1.819 ± 2.246 | 1.626 ± 3.953 | 0.718 ± 0.068 |
| H2-165 | 25 | 0.163 ± 0.011 | 1.812 ± 2.106 | 1.446 ± 0.972 | 1.057 ± 0.116 |
| H3-143 | 26 | 0.318 ± 0.004 | 1.744 ± 0.652 | 1.211 ± 0.464 | 1.470 ± 0.507 |
| H2-26 | 27 | 0.171 ± 0.004 | 1.705 ± 1.064 | 0.002 ± 0.458 | 1.646 ± 0.229 |
| H2-55 | 28 | 0.186 ± 0.012 | 1.549 ± 0.659 | 1.539 ± 0.351 | 1.463 ± 0.210 |
| H2-181 | 29 | 0.129 ± 0.003 | 1.426 ± 1.218 | 2.402 ± 1.318 | 0.820 ± 0.085 |
| H2-167 | 30 | 0.119 ± 0.010 | 1.399 ± 1.340 | 1.479 ± 2.434 | 1.704 ± 0.206 |
| H2-63 | 31 | 0.094 ± 0.005 | 1.304 ± 0.718 | 0.996 ± 0.302 | 0.851 ± 0.119 |
| H3-142 | 32 | 0.451 ± 0.036 | 1.287 ± 0.471 | 0.411 ± 0.492 | 1.145 ± 0.404 |
| H2-64 | 33 | 0.115 ± 0.011 | 1.268 ± 0.356 | 0.218 ± 1.157 | 1.485 ± 0.241 |

Total 108 unique variants are analyzed, and only representative variants are listed in the table. The 1st column from left shows the name assigned to the scFv variants; the 2nd column shows the sequence; the 3rd column shows the concentration of phage-free soluble scFv in culture supernatant; 4th-5th columns show the normalized neutralizing potency against BS/07 H1N1 and CA/09 H1N1 virus respectively; the 6th column shows the normalized binding affinity to BS/07 H1 HA. Three independent measurements were carried out to derive each averaged measurement and standard deviation for each of the scFv variants.

The germline sequence of F10 CDR-H2 is remarkably compatible with the sequence preference profiles of the scFv variants selected for high binding affinity or high neutralizing potency. The sequence profiles of the scFv variants selected for high binding affinity and high neutralizing potency were summarized in FIGS. 1A and 1B respectively, in which the normalized binding affinity score >0.3 (n=95, FIG. 1A), and the normalized neutralizing potency score >0.3 (n=41, FIG. 1B). Comparing these sequence profiles with the sequence profile of F10-CDRH2 scFvs randomly selected before selection/amplification cycles (data not shown) indicates that the sequence profiles in FIGS. 1A and 1B reflected the sequence requirements for binding and neutralization. Sequence preference biased due to structural requirements had been ruled out because scFvs selected for folding stability do not have any significant sequence preference in the CDRs. The similarity between the sequence profiles in FIGS. 1A and 1B indicated that the sequence requirements for binding were consistent with the sequence requirements for neutralization. In addition, the consensus sequence (S-P-M/L-F-N-Q, SEQ ID NOs: 69, 70) was strikingly similar to F10 CDR-H2 sequence (S-P-M-F-G-T, SEQ ID NO: 71), especially in the H52-H54 residue positions, again suggesting that the sequence of F10 CDR-H2 had largely reached the global neutralizing potency optimum targeting the highly conserved membrane-proximal epitope of IGHV1-69-bnAbs on the HA stem. The position specific scoring matrices (PSSMs) derived from the sequences of the scFv variants for which the sequence LOGOs were shown in FIGS. 1A and 1B were used to calculate the fitness scores of all human germline CDR-H2 sequences (Methods). The CDR-H2 sequence of IGHV1-69 gene appears as the only human germline CDR-H2 sequence that is positively compatible with the PSSMs (Table 3), explaining the observations that the highly conserved epitope patch in the stem region of HA (Table 1) can be optimally recognized with the CDR-H2 loop of the IGHV1-69 germline gene with only a few somatic mutations.

TABLE 3

PSSM and scoring of human CDRH2 H52-H56 sequences

| Germline | Score of PSSM with high neutralizing potency | Score of PSSM with high binding affinity |
|---|---|---|
| IGHV1-69 | 8.4 | 12.4 |
| IGHV1-69D | 8.4 | 12.4 |
| IGHV1-45 | −0.8 | −2.1 |
| IGHV1-8 | −6.0 | −4.8 |
| IGHV1-18 | −7.2 | −6.2 |
| IGHV3_OR16-8 | −7.2 | −10.9 |
| IGHV3_OR16-9 | −7.2 | −10.9 |
| IGHV5-10-1 | −9.3 | −13.7 |
| IGHV3-21 | −10.5 | −15.1 |
| IGHV3-30 | −10.5 | −16.8 |
| IGHV3-30-3 | −10.5 | −16.8 |
| IGHV3-11 | −11.0 | −16.2 |
| IGHV3-48 | −11.0 | −16.2 |
| IGHV1-38-4 | −11.2 | −8.6 |
| IGHV1-46 | −11.2 | −6.5 |
| IGHV1_OR15-5 | −11.2 | −10.7 |
| IGHV1_OR15-9 | −11.2 | −10.7 |
| IGHV1_OR21-1 | −11.2 | −10.7 |
| IGHV3-62 | −11.6 | −8.3 |
| IGHV3-23 | −12.4 | −12.1 |
| IGHV3-23D | −12.4 | −12.1 |
| IGHV3-43 | −12.4 | −14.2 |
| IGHV3-43D | −12.4 | −14.2 |
| IGHV3-64 | −12.4 | −14.2 |
| IGHV3-64D | −12.4 | −14.2 |
| IGHV3-9 | −12.4 | −14.2 |

TABLE 3-continued

PSSM and scoring of human CDRH2 H52-H56 sequences

| Germline | Score of PSSM with high neutralizing potency | Score of PSSM with high binding affinity |
|---|---|---|
| IGHV3-16 | −13.3 | −21.8 |
| IGHV3-19 | −13.3 | −21.8 |
| IGHV3-35 | −13.3 | −21.8 |
| IGHV1-2 | −14.0 | −14.0 |
| IGHV1-24 | −14.0 | −18.2 |
| IGHV1-69-2 | −14.0 | −18.2 |
| IGHV1_OR15-1 | −14.0 | −14.0 |
| IGHV1-68 | −14.0 | −12.4 |
| IGHV3_OR16-15 | −15.2 | −19.6 |
| IGHV3_OR16-16 | −15.2 | −19.6 |
| IGHV1_OR15-2 | −15.5 | −10.8 |
| IGHV7-4-1 | −15.5 | −12.2 |
| IGHV7-81 | −15.5 | −8.0 |
| IGHV5-51 | −17.3 | −24.5 |
| IGHV5-78 | −17.3 | −24.5 |
| IGHV1-3 | −19.2 | −19.2 |
| IGHV1-58 | −19.2 | −23.4 |
| IGHV1_OR15-3 | −19.2 | −19.2 |
| IGHV1_OR15-4 | −19.2 | −19.2 |
| IGHV3_OR16-12 | −19.9 | −20.6 |
| IGHV3-63 | −21.0 | −28.8 |
| IGHV3-33 | −22.4 | −29.8 |
| IGHV3-20 | −24.3 | −23.0 |
| IGHV3-74 | −27.6 | −29.4 |
| IGHV3-NL1 | −27.6 | −33.6 |
| IGHV3_OR16-13 | −27.6 | −29.4 |
| IGHV3_OR16-14 | −27.6 | −29.4 |
| IGHV3-52 | −30.4 | −39.0 |
| IGHV3-7 | −30.4 | −39.0 |

The 1st column from left shows the name of human germline. The scores of the human germline CDE-H2 sequences calculated with the PSSM constructed with the sequences of scFvs for which the normalized neutralizing potency greater than 0.3 are shown in 2nd column. The scores of the human germline CDR-H2 sequences calculated with the PSSM constructed with the sequences of scFvs for which the normalized binding affinity greater than 0.3 are shown in 3rd column.

Example 2 Global Search of the CDR-H1 Sequence of F10-Derived Binders Against the HA Yielded Less Well-Defined Sequence Preference Profiles Compatible with Many Human Germline VH Genes The sequence space of CDR-H1 for residue positions ranging from H24 to H32 in the F10 template was explored exhaustively in the F10-CDRH1 library. Two additional residue positions (H24-H25) were simultaneously explored along with the CDR-H1 region (H26-H32) defined by Chothia because the close proximity of the side chain in H24 to that of H26 in the type 1 canonical structure could influence the local conformation of the CDR-H1 loop. Since the CDR-H2 sequence was known to be optimized in F10 (see above), only the residue positions from H24 to H32 were diversified with the NNK degenerate codon in the F10-CDRH1 library with complexity >$10^9$ (FIG. 6); the sequence profile of randomly selected F10-CDRH1 scFvs did not show any significant biases due to phage library preparation (data not shown). The complexity limit of the F10-CDRH1 library is not enough to cover the theoretical gene diversity ($32^9$) of the experimental design. Still, the complexity of $10^9$ is sufficiently applicable to investigate cooperative combinations involving up to any 4 residues in 9 NNK-encoded residue positions ($32^4 \times 9!/5!/4!$). Given that most local sequence features involve one or two cooperatively dependent residues (as in tight turns and salt bridges), the library complexity should sustain the aim to explore globally optimal CDR-H1 sequences for the HA epitope of IGHV1-69-bnAbs to a large extent.

The maximal binding affinity of the selected scFv variants from the F10-CDRH1 library with immobilized BS/07 H1 HA were a few folds higher than that of F10 scFv; the neutralizing potencies of a few scFv variants against both BS/07 and CA/09 H1N1 viruses were slightly superior to that of F10 scFv. Again, the binding affinity of 78 selected scFv variants from the F10-CDRH1 library had no clear linear correlation ($r^2$<0.2) with their neutralizing potency against the corresponding influenza virus; the correlation of the neutralizing potencies against the two H1N1 influenza viruses were not obvious given the limitation of the experimental accuracy (data not shown). Total 78 scFv variants are analyzed. The sequences and the binding/neutralization data of the representative scFv variants are summarized in Table 4.

work. Nevertheless, the maximal affinity for the scFv variants shown in Table 4 indicated that many alternative contacts are equally adequate to provide favorable binding energy in place of those of F10 CDR-H1.

Figure 2A:
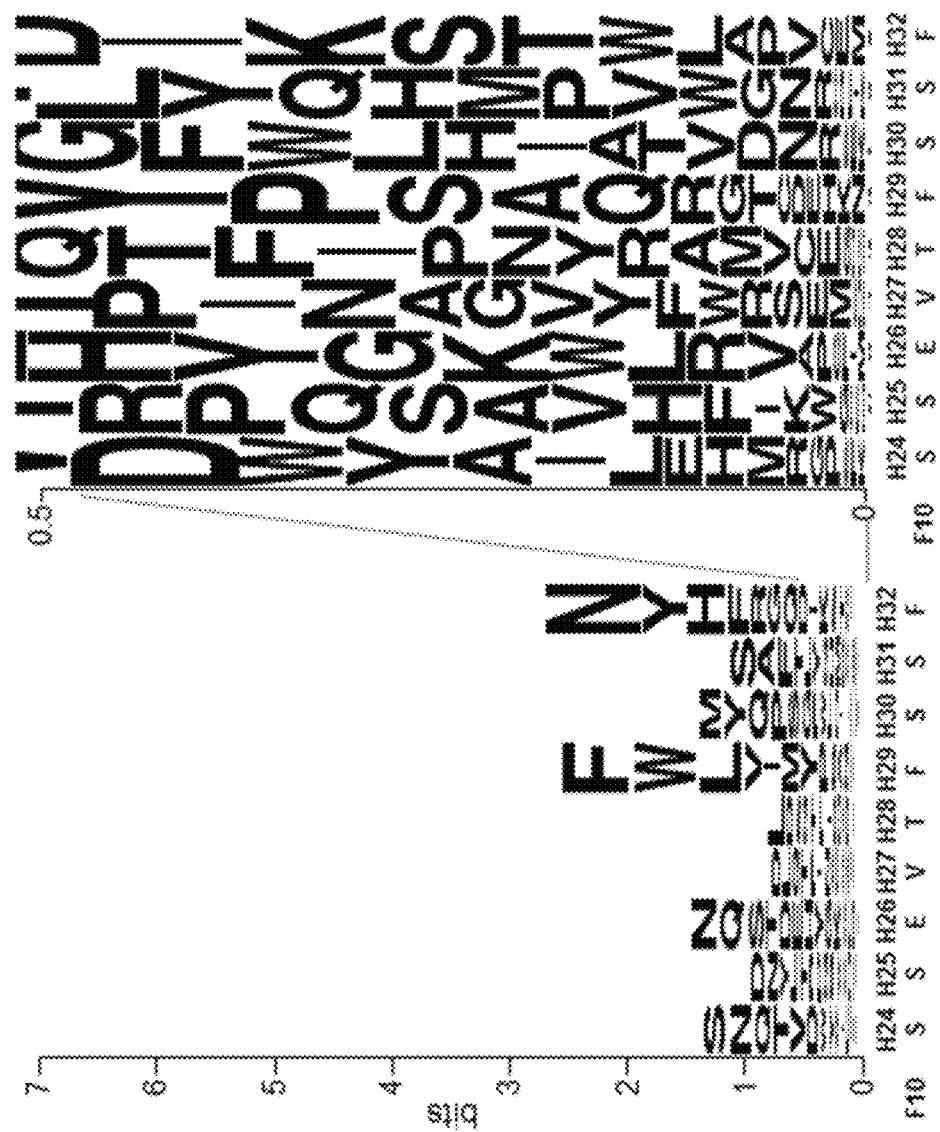
Figure 2B:
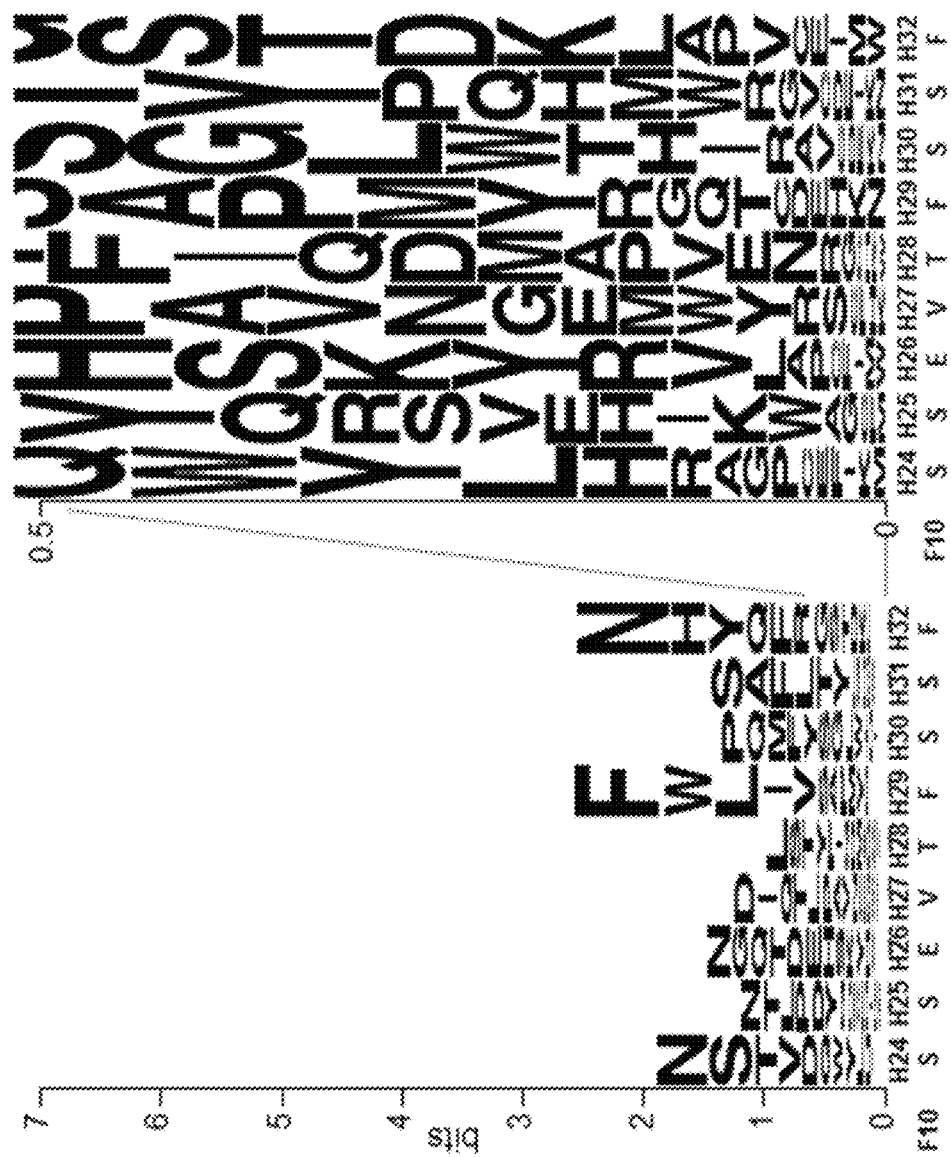

The sequence preference profiles shown in FIGS. 2A and 2B were not as compatible with the CDR-H1 germline sequence of IGHV1-69-bnAbs. Many other human germline CDR-H1 sequences were better compatible with the PSSMs derived from the selected scFv variants for which the sequence profiles were shown in FIGS. 2A and 2B. This result was in agreement with the conclusion of the previous paragraph that the F10 CDR-H1 local structure could be quite flexible to accommodate large number of alternative sequences that are equally effective in binding to the corresponding epitope on the HA stem, and as such, the CDR-H1

TABLE 4

Data for the representative scFv variants selected from the F10-CDRH1 library

| scFv | SEQ ID NO | concentration (μg/ml) | normalized neutralizing potency against BS/07 H1N1 | normalized neutralizing potency against CA/09 H1N1 | normalized binding affinity to BS/07 H1N1 |
|---|---|---|---|---|---|
| F10 | 65 | 1.347 ± 0.109 | 1.000 | 1.000 | 1.000 |
| H1-62 | 34 | 0.112 ± 0.008 | 7.476 ± 6.435 | 3.365 ± 2.008 | 2.628 ± 0.378 |
| H3-141 | 35 | 0.190 ± 0.001 | 2.782 ± 1.039 | 0.742 ± 1.201 | 2.728 ± 0.941 |
| H3-132 | 36 | 0.238 ± 0.052 | 2.172 ± 0.967 | 1.701 ± 0.731 | 1.701 ± 0.704 |
| H1-74 | 37 | 0.098 ± 0.020 | 2.111 ± 1.859 | 1.274 ± 1.219 | 1.047 ± 0.394 |
| H1-82 | 38 | 0.089 ± 0.009 | 1.380 ± 1.559 | 1.494 ± 1.345 | 2.662 ± 0.365 |
| H1-81 | 39 | 0.080 ± 0.002 | 1.337 ± 1.975 | 2.470 ± 1.794 | 0.951 ± 0.087 |
| H1-80 | 40 | 0.088 ± 0.003 | 1.234 ± 1.535 | 0.768 ± 2.258 | 1.092 ± 0.173 |
| H1-83 | 41 | 0.164 ± 0.013 | 1.088 ± 1.090 | 0.380 ± 1.816 | 1.302 ± 0.223 |
| H3-136 | 42 | 0.275 ± 0.007 | 1.087 ± 0.467 | 0.397 ± 0.814 | 1.289 ± 0.464 |
| H3-139 | 43 | 0.288 ± 0.028 | 1.075 ± 0.467 | 0.615 ± 0.728 | 1.373 ± 0.492 |

Total 78 unique variants are analyzed, and only representative variants are listed in the table. The $1^{st}$ column from left shows the name assigned to the scFv variants; the $2^{nd}$ column shows the sequence; the $3^{rd}$ column shows the concentration of phage-free soluble scFv in culture supernatant; $4^{th}$-$5^{th}$ columns show the normalized neutralizing potency against BS/07 H1N1 and CA/09 H1N1 virus respectively; the $6^{th}$ column shows the normalized binding affinity to BS/07 H1 HA. Three independent measurements were carried out to derive each averaged measurement and standard deviation for each of the scFv variants.

Figure 1B:
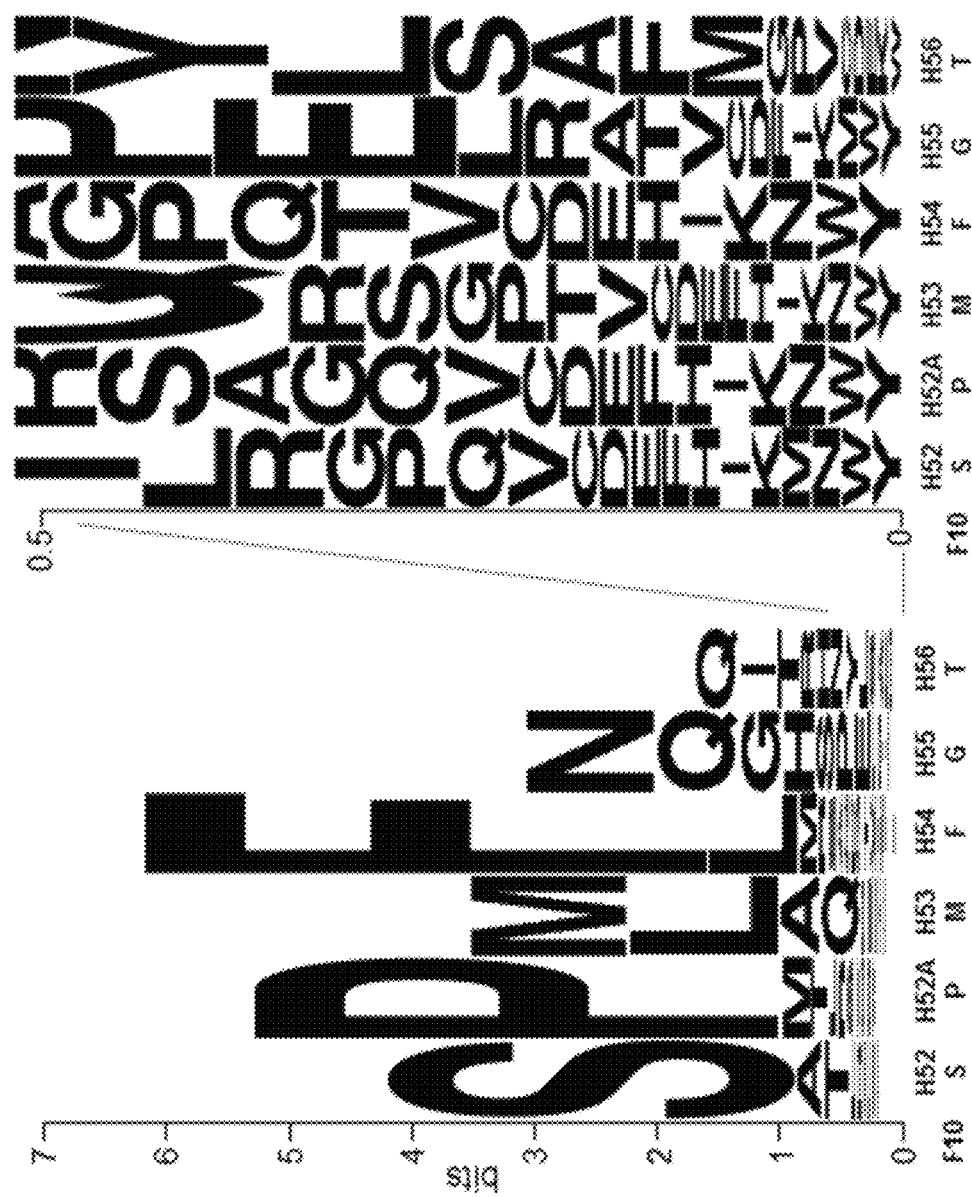

The sequence profiles of the scFv variants selected for high binding affinity and high neutralizing potency, as summarized in FIGS. 2A and 2B respectively, did not shown strong preferences for amino acid types in all the residue positions explored. In these figures, the normalized binding affinity score >0.3 (n=62, FIG. 2A), and the normalized neutralizing potency score >0.3 (n=37, FIG. 2B). The most conserved residue position was H29, for which the aromatic/hydrophobic side chain is expected to stabilize the type 1 canonical structure of the CDR-H1 loop by packing with the upper hydrophobic core of the VH domain. The other conserved residue position is H32, where the aromatic/hydrophilic side chain is in contact with the membrane-distal epitope on HA stem. Overall, the similarity between the sequence profiles indicated that the sequence requirements for binding are consistent with the sequence requirements for neutralization, but the lack of sequence preferences in the sequence profiles for CDR-H1 shown in FIGS. 2A and 2B were in sharp contrast to the well-defined sequence preference profiles for CDR-H2 (FIGS. 1A and 1B). The lack of prominent sequence preferences in the CDR-H1 region was unexpected, judging by the extensive intermolecular hydrogen bonding involving the side chains of Thr28, Ser30 and Ser31 and the hydrophobic/aromatic interactions involving the side chains of Val27 and Phe32 in the F10-HA complex structure. The discrepancy could be attributed to that the H3 HA structure in the F10-HA complex structure might not reflect the structural contacts relevant to the interactions between F10 and H1 HA in this sequences could be specific to the HA mutations in the corresponding epitope. The flexibility of CDR-H1 was advantageous to accommodate the less conserved membrane-distal patch of epitope in the HA stem (Table 1).

Example 3 Global Search of the CDR-H3 Sequence of F10 Revealed the Prominent Role of Tyr98 and Pro96 in Assistance of CDR-H2 Recognizing Conserved the HA Stem Epitope The sequence space of CDR-H3 for residue positions ranging from H96 to H100E in the F10 template was explored exhaustively in the F10-CDRH3 library with complexity >$10^9$; the sequence profile of randomly selected F10-CDRH3 scFvs did not show any significant biases due to phage library preparation (data not shown). The aim was to explore globally optimal CDR-H3 sequences that are in contact with the HA epitope of IGHV1-69-bnAbs. Again, the maximal binding affinity of the selected scFv variants from the F10-CDRH3 library was a few folds higher than that of F10 scFv; the neutralizing potencies of a few scFv variants against both BS/07 and CA/09 H1N1 viruses were only marginally superior to that of F10 scFv. The binding affinity of 201 selected scFv variants from the F10-CDRH3 library had no clear linear correlation ($r^2$<0.1) with their neutralizing potency against the corresponding influenza virus; the neutralizing potencies against the two influenza viruses were marginally correlated ($r^2$=0.41) at best considering the experimental error (data not shown). Total 201 scFv variants are analyzed. The sequences and the binding/neutralization data of representative scFv variants are summarized in Table 5. The sequence profiles of the scFv variants selected for high binding affinity and high neutralizing potency were summarized in FIGS. 3A and 3B respectively, in which the normalized binding affinity score >0.3 (n=140, FIG. 3A), and the normalized neutralizing potency score >0.3 (n=77, FIG. 3B). The conserved residue position Tyr98 aromatic side chain is expected to augment the CDR-H2 recognition of the highly conserved epitope in the HA stem by contacting the aliphatic atoms on Thr41 and Ile45 of HA2. Pro96 was also highly conserved. This residue does not contact with the antigen and could support the rigidity of the CDR-H3 loop structure, which in turn sustain the contact position of the side chain of Tyr98. Phage library preparation biases (data not shown) and structural preferences have been ruled out from accounting for the sequence preferences of Pro96 and Tyr98. The other CDR-H3 positions are not in contact with HA, and thus the preference profiles were not expected to be well-defined. However, it was unexpected that the disulfide bond Cys100-Cys100E in F10 was not conserved, although disulfide bonds in CDR-H3 are frequently required for antigen recognition. The results suggested that the F10 CDR-H3 local structure could be also quite flexible to accommodate alternative sequences, as long as the key residue Tyr98 is in proper contact, perhaps assisted by Pro96, with the corresponding epitope.

strains of influenza virus scattered between 0 and 2 (FIG. 4B, x-axis), indicating that the improvement of binding affinity and neutralizing potency of an antibody against one virus strain were likely to lead to improvement of binding affinity to the other strain but not necessarily lead to improvement of neutralizing potency.

The scFvs selected from the F10-CDRH1~3 synthetic antibody libraries were specific only to the H1 HAs. Synthetic antibodies are not negatively selected by immune system and thus could cross-react to irrelevant antigens. To investigate the cross-reactivity for the scFvs selected from the F10-CDRH1~3 scFv libraries, we randomly selected 10, 6, and 14 scFvs from Tables 4, 2 and 5, respectively, and measured the binding of these scFvs to H1 HAs, H3 HAs, other diverse human proteins and DNA. None of the selected scFvs bound to antigens other than CA/09 H1 HA and BS/07 H1 HA (data not shown), suggesting that the selected scFvs from the F10-CDRH1~3 scFv libraries were specific only to H1 HAs. This specificity was in agreement with that of the parent template F10, which only bound to group 1 HAs (such as H1 HAs) but not group 2 HA (such as H3 HAs). The averaged affinity for the representative scFvs binding to BS/07 H1 HA was higher than that binding to CA/09 H1 HA because these scFvs were selected against immobilized BS/07 H1 HA.

TABLE 5

Data for the representative scFv variants selected from the F10-CDRH3 library

| scFv | SEQ ID NO | concentration (μg/ml) | normalized neutralizing potency against BS/07 H1N1 | normalized neutralizing potency against CA/09 H1N1 | normalized binding affinity to BS/07 H1N1 |
|---|---|---|---|---|---|
| F10 | 65 | 1.347 ± 0.109 | 1.000 | 1.000 | 1.000 |
| H3-268 | 44 | 0.075 ± 0.004 | 8.021 ± 6.038 | 8.040 ± 10.606 | 2.694 ± 0.392 |
| H3-48 | 45 | 0.093 ± 0.004 | 7.815 ± 7.027 | 6.129 ± 2.363 | 0.339 ± 0.040 |
| H3-188 | 46 | 0.033 ± 0.004 | 2.193 ± 2.729 | 5.330 ± 3.142 | 12.603 ± 1.531 |
| H3-172 | 47 | 0.164 ± 0.044 | 2.153 ± 1.121 | −0.088 ± 1.533 | 1.782 ± 0.479 |
| H3-49 | 48 | 0.151 ± 0.005 | 1.966 ± 1.815 | 1.471 ± 1.449 | 0.129 ± 0.014 |
| H3-61 | 49 | 0.132 ± 0.013 | 1.708 ± 0.397 | 1.549 ± 0.944 | 1.811 ± 0.399 |
| H3-205 | 50 | 0.223 ± 0.030 | 1.691 ± 0.503 | −0.216 ± 1.284 | 2.367 ± 0.324 |
| H3-182 | 51 | 0.334 ± 0.008 | 1.654 ± 0.170 | 1.468 ± 0.221 | 1.882 ± 0.061 |
| H3-219 | 52 | 0.301 ± 0.041 | 1.480 ± 0.283 | 1.783 ± 0.351 | 1.679 ± 0.234 |
| H3-186 | 53 | 0.417 ± 0.031 | 1.460 ± 0.135 | 0.664 ± 0.229 | 1.520 ± 0.120 |

Total 201 unique variants are analyzed, and only representative variants are listed in the table. The $1^{st}$ column from left shows the name assigned to the scFv variants; the $2^{nd}$ column shows the sequence; the $3^{rd}$ column shows the concentration of phage-free soluble scFv in culture supernatant; $4^{th}$-$5^{th}$ columns show the normalized neutralizing potency against BS/07 H1N1 and CA/09 H1N1 virus respectively; the $6^{th}$ column shows the normalized binding affinity to BS/07 H1 HA. Three independent measurements were carried out to derive each averaged measurement and standard deviation for each of the scFv variants.

Figure 3A:
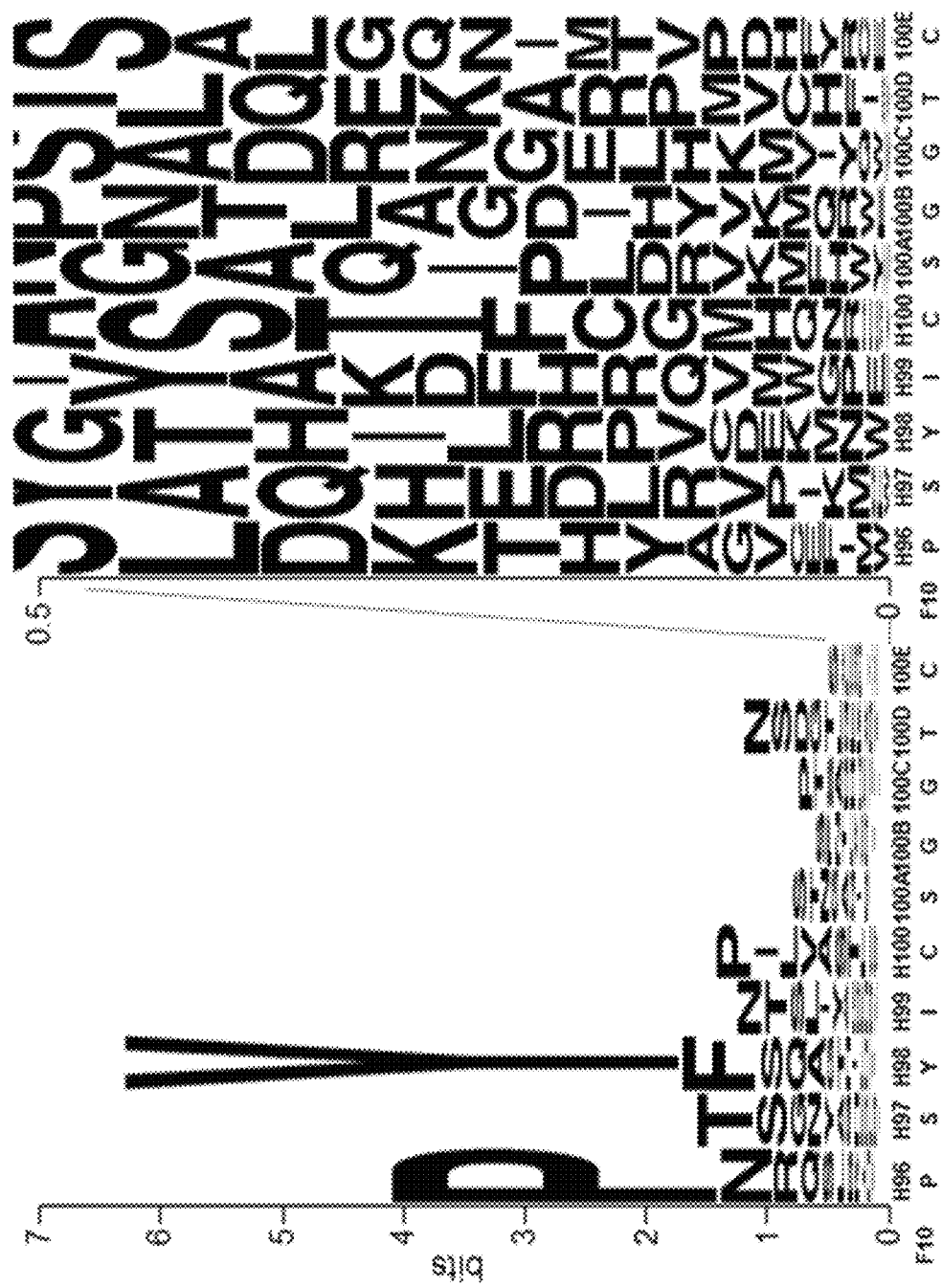
Figure 3B:
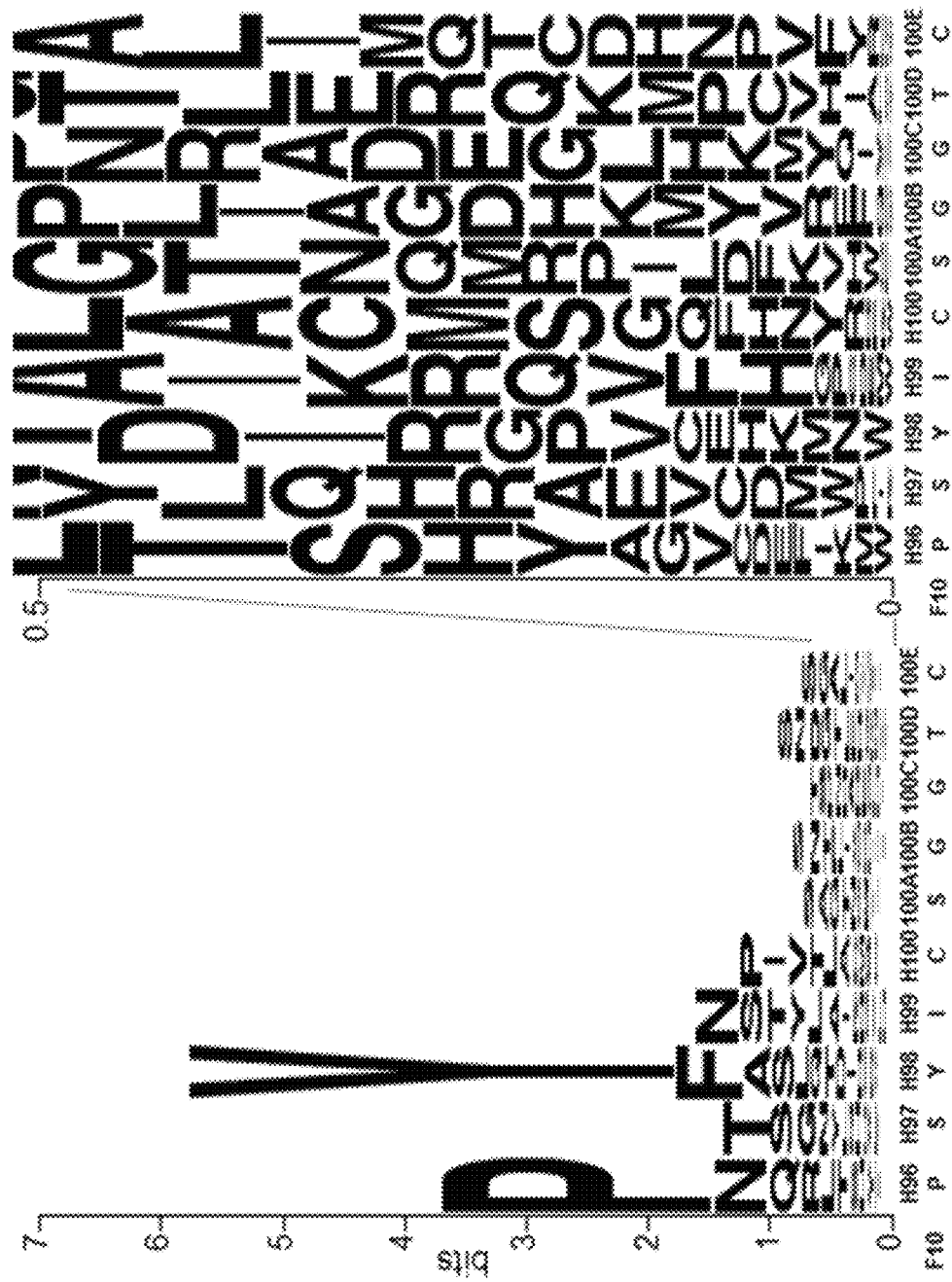
Figures 4A, 4B:
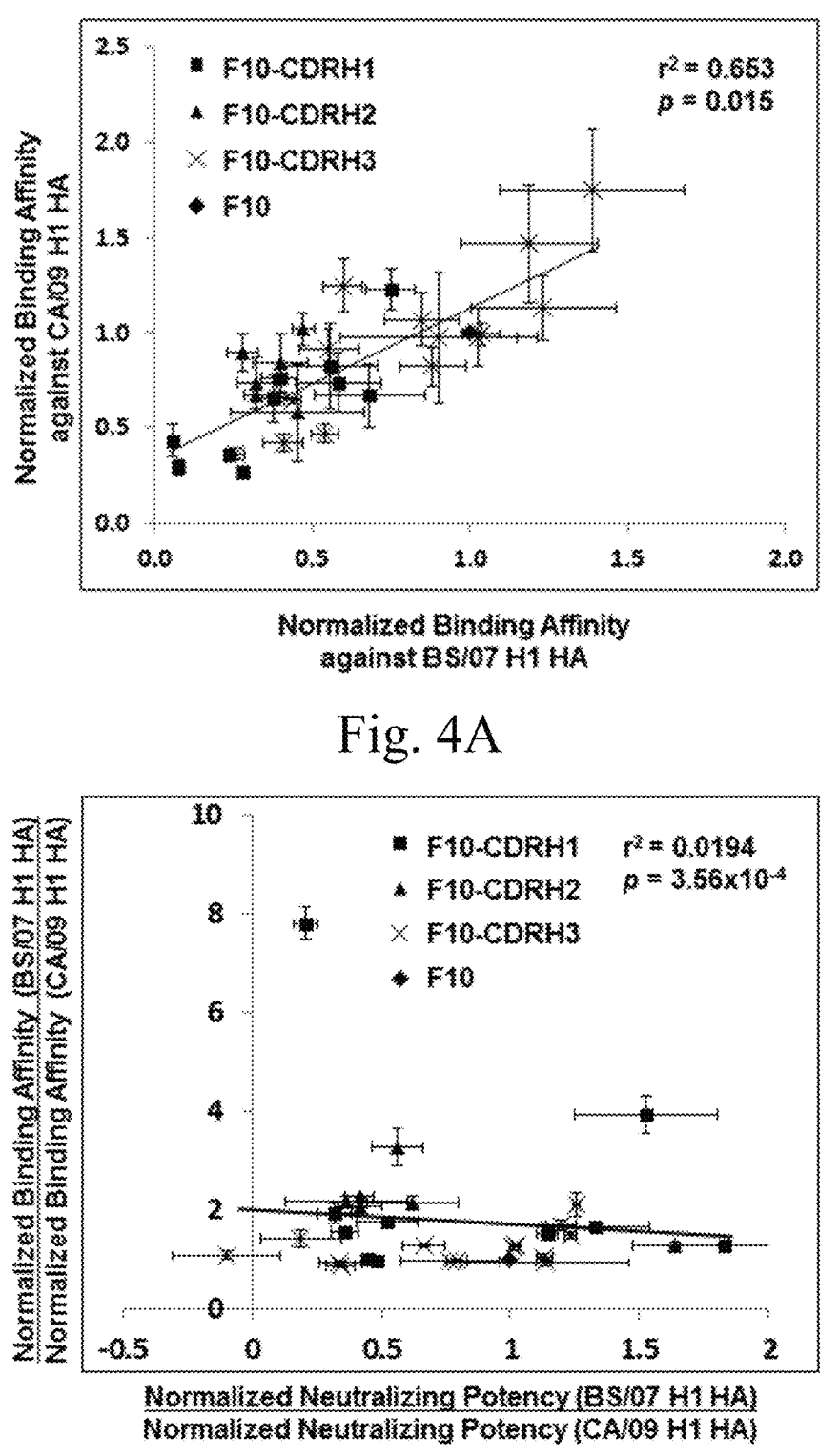
Figure 6:
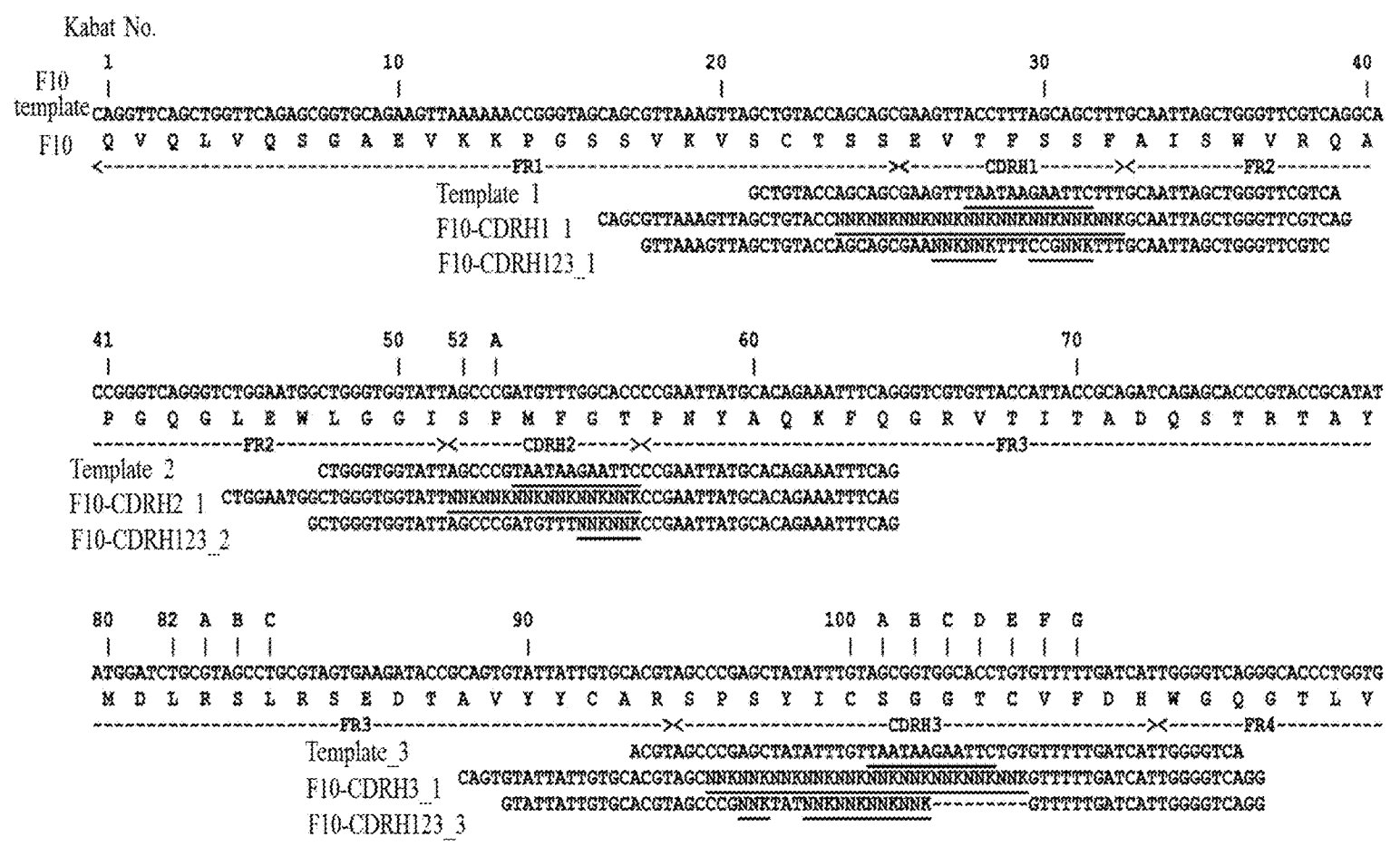

Example 4 H1 HA-Binding scFvs Selected from F10-CDRH1~3 Libraries Bound to the H1 HAs with Correlation but Did not Cross-React to H3 HA or Other Human Antigens The normalized binding affinities of scFvs from library F10-CDRH1~3 had strong linear correlation in binding to CA/09 H1 HA and BS/07 H1 HA, but the correlated improvement of affinity against both strains of virus did not necessarily imply that the gain of the neutralizing potency against the two strains of virus are correlated. FIG. 4A showed the strong correlation of the normalized binding affinity for randomly selected scFvs from the three synthetic antibody libraries against the two H1 HAs, explaining that the ratios of the normalized binding affinities for the two H1 HAs were centered near 1~2 (FIG. 4B, y-axis). However, the ratios of the normalized neutralizing potency against the two Example 5 Antibody Library Designed with Information from the Antibodies Binding to BS/07 H1 HA can be Used to Discover Potent Neutralizing Antibodies Targeting the Corresponding Stem Epitope on CA/09 H1 HA The results above (FIGS. 1-4) informed an antibody library design aiming at generating specific and optimal neutralizing antibodies targeting the corresponding stem epitope on diverse strains of H1 HA. FIG. 6 showed the F10-CDRH123 antibody library design, where the CDR-H2 residues Ser52-Pro52A-Met53-Phe54 (SEQ ID NO: 72) and CDR-H3 residues Pro96 and Tyr98 were fixed for optimal binding to the highly conserved membrane-proximal epitope patch on the HA stem. Met53 and Phe54 made key contacts with the HA epitope (FIGS. 1A and 1B). Ser52 did not contact the antigen, but the hydroxyl side chain forms hydrogen bond with the backbone carboxyl group of Tyr98, likely to stabilize the core paratope structure. Pro52A was encoded in IGHV1-69 gene and could be responsible for the rigidity of the CDR-H2 loop structure. Residue position Phe29 was fixed to stabilize the CDR-H1 type 1 canonical structure; Pro30 was fixed to interact with the largely hydrophobic membrane-distal epitope patch on the HA stem and also to reduce the conformational entropy penalty of the CDR-H1 loop upon binding to the epitope; F32 was fixed to aid the possible hydrophobic interactions with hydrophobic residues in the membrane-distal epitopes of H1 HAs. The CDR-H1 residue positions H27, H28, H31 were expected to contact with the less conserved membrane-distal epitope and thus were diversified with degenerate codon NNK. The other unfixed residue positions were also diversified because of their vicinity to the fixed residue positions and their likelihood to interact, albeit marginally, with the HA stem epitope. In addition, the CDR-H3 sequence length in the F10-CDRH123 library was fixed at 12 residues as in CR6261 and CR9114 without the disulfide bond as in F10. The disulfide bond was not expected to be critical for antigen recognition, as revealed in the results above (FIGS. 3A and 3B). The aim of the F10-CDRH123 library was to explore globally optimal sequences targeting the epitope of IGHV1-69-bnAbs in diverse strains of HA.

The phage-displayed F10-CDRH123 antibody library was constructed (FIG. 6) to the complexity >$10^9$ without significant biases due to phage library preparation (data not shown). The library was tested for neutralizing antibody discovery against CA/09 H1N1 influenza virus. The experiment was designed to test the rationale that a library designed with the information arrived with one strain of H1 HA (BS/07, FIGS. 1-3) is equally applicable of discovering optimal binder and neutralizer against another strain of H1 HA (CA/09 in this case). More than 1000 scFvs binding to immobilized CA/09 H1 HA were discovered after three rounds of phage display selection-amplification cycle. All these selected scFvs competed with F10 scFv for binding to HA, indicating that all these scFvs bound to the common epitope of IGHV1-69-bnAbs. The binding affinities of a large portion of the selected scFvs were a few folds higher than that of F10 scFv. Unlike the results from the F10-CDRH1~3 libraries, the binding affinities of the scFv variants from the F10-CDRH123 library were overall correlated to an extent ($r^2$=0.39, p-value=$10^{-29}$) with their neutralizing potencies against CA/09 H1N1 influenza virus, suggesting that the conformational uncertainty could be partially alleviated by the constant residues in the key CDR positions. By contrast to the marginal improvement in neutralizing potencies shown in FIGS. 1-3, the neutralizing potencies of a large portion of the selected scFv variants against CA/09 H1N1 virus were superior to that of F10 scFv (data not shown). These results indicated that simultaneous diversification of the residues in all CDRs are necessary to cooperatively optimize the binding affinity and neutralizing potency.

We measure the $EC_{50}$ and $IC_{50}$ for the purified scFvs, and the $EC_{50}$ and $IC_{50}$ for a tiny portion of the scFvs were measured (Table 6), because the expression and purification of the scFvs (Materials and Methods) and the measurements of $EC_{50}$ and $IC_{50}$ (Materials and Methods) are labor- and resource-intensive. Nevertheless, the $EC_{50}$ for CA/09 H1 HA and $IC_{50}$ for CA/09 H1N1 virus for randomly selected scFvs were marginally correlated to an extent (Table 6).

TABLE 6

Data for the purified scFv variants selected from the F10-CDRH123 library

| scFv | SEQ ID NO | $IC_{50}$ against CA/09 H1N1 (ng/ml) | $EC_{50}$ against CA/09 H1 HA (ng/ml) |
|---|---|---|---|
| F10 | 65 | 202.71 ± 6.30 | 22.54 ± 2.06 |
| H123#437 | 54 | 130.54 ± 10.97 | 18.06 ± 4.06 |
| 1101-178 | 55 | 163.66 ± 14.09 | 20.87 ± 2.00 |
| 3rd_0.5_4_09H | 56 | 109.50 ± 5.43 | 10.18 ± 0.31 |
| 3rd_0.5_2_2A | 57 | 142.72 ± 2.55 | 11.95 ± 3.03 |
| 1101-181 | 58 | 204.79 ± 11.96 | 110.99 ± 10.39 |
| H123#425 | 59 | 194.87 ± 21.34 | 136.95 ± 6.50 |
| 3rd_1-4-B-02 | 60 | 232.94 ± 10.43 | 14.06 ± 2.22 |
| 1101-150 | 61 | 135.65 ± 1.50 | 29.97 ± 1.05 |
| 1026B52 | 62 | 74.41 ± 2.73 | 6.28 ± 0.83 |
| 1026R66 | 66 | 106.70 ± 3.10 | 24.51 ± 0.89 |
| 1026B77 | 63 | 65.30 ± 5.50 | 9.01 ± 2.46 |
| 1101-170 | 64 | 170.30 ± 4.64 | 14.75 ± 0.09 |

The 1st column from left shows the name assighned to the scFv variants; the 2nd column shows the amino acid sequence of specified scFv variant; the 3rd and 4th columns show $IC_{50}$ against CA/09 H1N1 virus infection and $EC_{50}$ binding to CA/09 H1 HA, respectively. At least three independent measurements were carried out to derive each averaged measurement and standard deviation for each of the scFv variants.

Figure 5A:
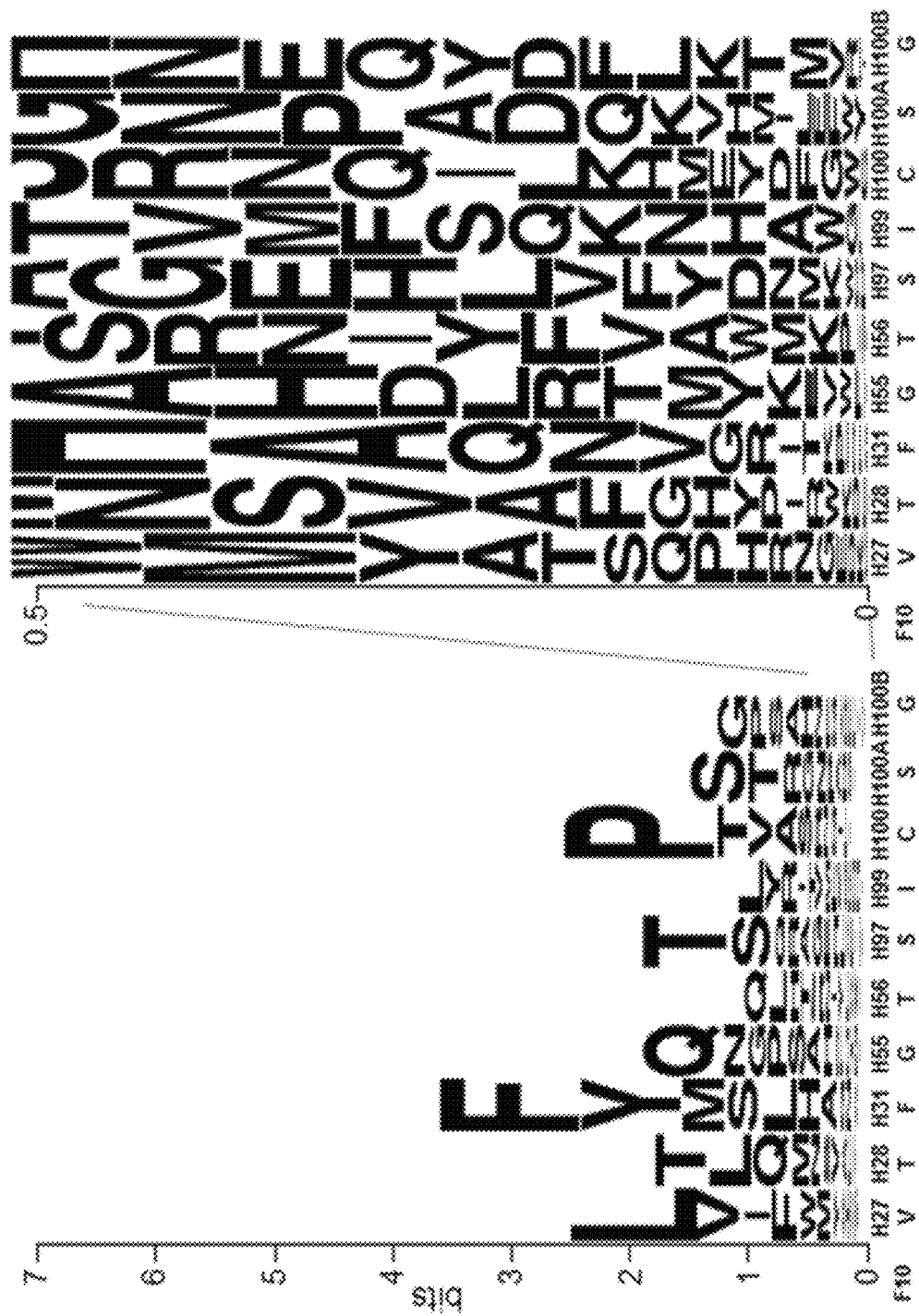
(FIG. 5A) The sequence LOGO was calculated from 976 CDR-H123 sequences with the normalized binding affinity greater than 0.3, in which the left panel represents the sequence LOGO with y-axis ranging from 0 to 7 bits, and the right panel provides the magnified view of the left panel that represents the sequence LOGO displayed between 0 and 0.5 bits.
Figure 5B:
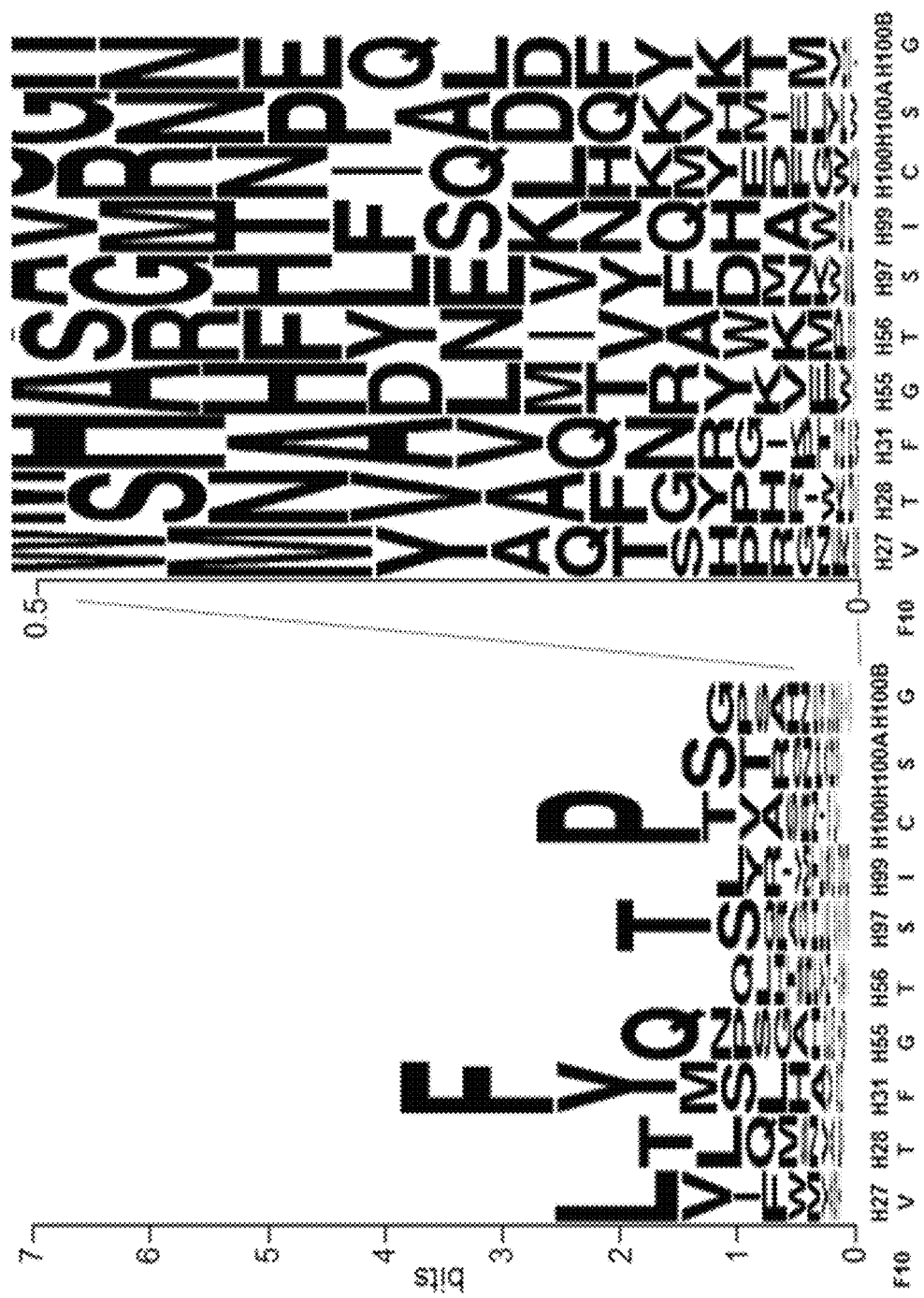
(FIG. 5B) The sequence LOGO was calculated from 750 CDR-H123 sequences with the normalized neutralizing potency greater than 0.3, in which the left panel represents the sequence LOGO with y-axis ranging from 0 to 7 bits, and the right panel provides the magnified view of the left panel that represents the sequence LOGO displayed between 0 and 0.5 bits. Both LOGOs were calculated with the background probabilities based on the degenerate codon NNK. The data of representative variants are summarized in Table 7.

The sequence profiles of the selected scFv variants were summarized in FIGS. 5A and 5B, in which the normalized binding affinity score >0.3 (n=976, FIG. 5A), and the normalized neutralizing potency score >0.3 (n=750, FIG. 5B). Total 1049 scFv variants are analyzed. The sequences and the binding/neutralization data of representative scFv variants are summarized in Table 7. The moderately conserved hydrophobic residues in H27 and H31 were expected due to the hydrophobic interactions with the membrane-distal hydrophobic epitope patch. The preference of Pro at H100 is consistent with similar findings previously. Similar to the results shown in FIGS. 1-3, the sequence preference profiles for the other CDR positions in FIGS. 5A and 5B were only moderately conserved at best, confirming that the amino acid types of these positions are not critically restricted for the antigen recognition.

TABLE 7

Data for the representative scFv variants selected from the F10-CDRH123 library

| scFv | SEQ ID NO | concentration (μg/ml) | normalized neutralizing potency against CA/09 H1N1 | normalized binding affinity against CA/09 H1 HA |
|---|---|---|---|---|
| F10 | 65 | 1.174 ± 0.043 | 1.000 | 1.00 |
| H123#437 | 54 | 0.183 ± 0.006 | 3.487 ± 0.893 | 5.158 ± 0.475 |
| 3rd_1-4-B-02 | 60 | 0.167 ± 0.003 | 3.350 ± 0.862 | 4.568 ± 0.420 |
| 1101-150 | 61 | 0.310 ± 0.002 | 3.318 ± 1.006 | 3.559 ± 0.764 |
| 1026B52 | 62 | 0.277 ± 0.005 | 2.976 ± 0.484 | 3.765 ± 0.327 |
| 1101-178 | 55 | 0.313 ± 0.029 | 2.804 ± 1.170 | 3.903 ± 0.736 |
| 1101-170 | 64 | 0.350 ± 0.019 | 2.706 ± 0.836 | 2.788 ± 0.519 |
| 3rd_0.5-4-09H | 67 | 0.441 ± 0.016 | 2.664 ± 0.561 | 2.459 ± 0.387 |
| 1026B77 | 63 | 0.327 ± 0.013 | 2.472 ± 0.374 | 3.993 ± 0.392 |
| 3rd_0.5-2-2A | 68 | 0.451 ± 0.019 | 2.462 ± 0.476 | 2.762 ± 0.420 |
| 1101-181 | 58 | 0.333 ± 0.018 | 2.338 ± 1.096 | 2.750 ± 0.472 |
| H123#425 | 59 | 0.215 ± 0.008 | 2.322 ± 0.832 | 3.094 ± 0.292 |

Total 1049 unique variants are analyzed, and only representative variants are listed in the table. The 1st column from left shows the name assigned to the scFv variants; the 2nd column shows the amino acid sequence of specified scFv variant; the 3rd column shows the concentration of phage-free soluble scFv in culture supernatant; 4th-5th columns show the normalized neutralizing potency and normalized binding affinity against CA/09 H1N1 virus and CA/09 H1 HA, respectively. Three independent measurements were carried out to derive each averaged measurement and standard deviation for each of the scFv variants.

IgG constructed based on the best of the selected scFv variants from F10-CDRH123 was demonstrated to gain neutralizing potency against the influenza virus infection by 3~7 folds depending on the H1N1 virus strains. H123#437 scFv (highlighted in bold in Table 6) had the highest normalized binding affinity (5.2±0.5) and second highest normalized neutralizing potency (3.5±0.9) among the selected scFvs. The H123#437 IgG constructed based on the H123#437 scFv neutralized CA/09 H1N1 infection with $IC_{50}$ of 269±4 ng/ml, which was about 3 folds more potent than that of the F10 IgG ($IC_{50}$=810±110 ng/ml) against the infection of the same H1N1 virus, confirming the anticipated improvement in neutralizing potency of the H123#437 scFv. Moreover, the H123#437 IgG neutralized BS/07 H1N1 infection with $IC_{50}$ of 232±1 ng/ml, which was about 7 folds more potent than that of the F10 IgG ($IC_{50}$=1847±311 ng/ml) against the infection of the same H1N1 virus. This improvement is remarkable in that the F10 IgG had already been refined to sub nano-M affinity through natural affinity maturation. These results indicate that the neutralizing potency of F10 can be further optimized specific to the strain of the antigen HA by modifying the amino acid sequences surrounding the key CDR residues; different H1N1 strain could require different combination of the peripheral amino acids to fine-tune the neutralizing potency and binding affinity.

The binding affinities of F10 IgG and H123#437 IgG to both BS/07 H1 HA and CA/09 H1 HA were about the same. The range of $EC_{50}$'s was from 2.5 to 2.9 ng/mL. The dissociation constant ($K_D$) measured by BIACORE was 46 pM for F10 IgG binding to CA/09 H1 HA ($k_{on}$=2.40×10$^5$ (1/Ms); $k_{off}$=1.11×10$^{-5}$ (1/s)), which was slightly better than the $K_D$ for H123#437 IgG binding to the same antigen ($K_D$=91 pM; $k_{on}$=3.86×10$^5$ (1/Ms); $k_{off}$=3.52×10$^{-5}$ (1/s)). Although the $K_D$ measurements were consistent with the $EC_{50}$ measurements within the range of experimental error, these results did not match with the measurement that the normalized binding affinity of H123#437 scFv was about 5 folds better than that of F10 scFv. Minor structural differences of the VH domains in the scFv and IgG could lead to the $k_{off}$ for the H123#437 IgG a few folds faster than anticipated.

Results indicate that a pair of neutralizing antibodies with similar affinity binding to two strains of HA could have substantially different neutralizing potency against the two corresponding strains of influenza virus. The two antibodies (F10 IgG and H123#437 IgG) are highly related in sequence and bind to the same epitope of HA with similar $EC_{50}$ to CA/09 H1 HA and BS/07 H1 HA, but the neutralizing potency ($IC_{50}$) for H123#437 IgG is 3~7 folds more potent than that of F10 IgG against the two strains of influenza virus, suggesting that although the general positive linear correlation between the binding affinity and neutralizing potency did exist to an extent, the affinity-function correlation was not applicable universally—affinity optimization alone does not necessarily lead to functionally optimized IgG antibodies.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A phage-displayed single-chain variable fragment (scFv) library comprising a plurality of scFvs that are expressed by a phage and exhibit binding affinity and specificity to an H1 hemagglutinin of influenza virus, wherein the plurality of scFvs respectively comprises the amino acid sequences of SEQ ID NOs: 24-26, 34-37 and 44-46.

2. The phage-displayed scFv library of claim 1, wherein the phage is a M13 phage or a T7 phage.

3. A method for selecting one phage-displayed scFv from the phage-displayed scFv library of claim 1, wherein the phage-displayed scFv exhibits high affinity and specificity to the H1 hemagglutinin, comprising, (a) incubating the phage-displayed scFv library of claim 1 with the H1 hemagglutinin, wherein the phage-displayed scFv library comprises a plurality of phage-displayed scFvs;

(b) subjecting the product of step (a) to an acid treatment thereby producing a plurality of phage-displayed scFvs, which are respectively bound to the H1 hemagglutinin before the acid treatment;

(c) subjecting the plurality of phage-displayed scFvs produced in the step (b) to an alkaline treatment; and (d) repeating at least one run of the steps (b) and (c), each time using the product of the step (c) in previous run as the phage library for incubating with the H1 hemagglutinin, until the phage-displayed scFv exhibiting the highest binding affinity and specificity to the H1 hemagglutinin is obtained.

4. A phage-displayed scFv selected from the phage-displayed scFv of claim 1, comprising the amino acid sequence of any of SEQ ID NOs: 24-26, 34-37 and 44-46.

5. A method of producing a recombinant antibody from the phage-displayed scFv library of claim 1 that exhibits binding affinity and specificity to the H1 hemagglutinin, comprising, (a) incubating the phage-displayed scFv library of claim 1 with the H1 hemagglutinin, wherein the phage-displayed scFv library comprises a plurality of scFvs;

(b) selecting phages that express scFvs with binding affinity and specificity to the H1 hemagglutinin;

(c) expressing the scFvs of the selected phages in the step (b) as soluble forms;

(d) selecting the soluble scFv of the step (c) that exhibits the highest binding affinity and specificity to the H1 hemagglutinin;

(e) extracting a phagemid DNA that corresponds to the selected soluble scFv of the step (d);

(f) respectively amplifying a first nucleic acid sequence that encodes a first polypeptide comprising CDR-H1, CDR-H2, and CDR-H3, and a second nucleic acid sequence that encodes a second polypeptide comprising CDR-L1, CDR-L2, and CDR-L3 by PCR using the phagemid DNA of step (e) as a template;

(g) respectively inserting the first and second nucleic acid sequences into an expression vector that comprises a third and a fourth nucleic acid sequences, wherein the third nucleic acid sequence encodes a third polypeptide comprising the constant regions of a heavy chain of an immunoglobulin, and the fourth nucleic acid sequence encodes a fourth polypeptide comprising the constant regions of a light chain of the immunoglobulin; and (h) transfecting a host cell with the expression vector of step (g) comprising the first, second, third, and fourth nucleic acid sequences so as to produce the antigen-specific recombinant antibody.

6. The method of claim 5, wherein the first nucleic acid sequence is disposed at the upstream of the third nucleic acid sequence, and the second nucleic acid sequence is disposed at the upstream of the fourth nucleic acid sequence.

7. The method of claim 5, wherein the immunoglobulin is selected from the group consisting of immunoglobulin G (IgG), immunoglobulin A (IgA), immunoglobulin D (IgD), immunoglobulin E (IgE), and immunoglobulin M (IgM).

8. The method of claim 5, wherein the host cell is a mammalian cell.

* * * * *